(12) United States Patent
Lin

(10) Patent No.: US 11,414,765 B2
(45) Date of Patent: Aug. 16, 2022

(54) ION-EXCHANGE MEMBRANE ELECTROLYSIS DEVICE

(71) Applicant: Hsin-Yung Lin, Shanghai (CN)

(72) Inventor: Hsin-Yung Lin, Shanghai (CN)

( * ) Notice: Subject to any disclaimer, the term of this patent is extended or adjusted under 35 U.S.C. 154(b) by 628 days.

(21) Appl. No.: 16/505,777

(22) Filed: Jul. 9, 2019

(65) Prior Publication Data
US 2020/0017981 A1 Jan. 16, 2020

(30) Foreign Application Priority Data

Jul. 10, 2018 (CN) .......................... 201810752166.7

(51) Int. Cl.
*C25B 1/04* (2021.01)
*C25B 15/08* (2006.01)
(Continued)

(52) U.S. Cl.
CPC ............... *C25B 1/04* (2013.01); *A61K 9/007* (2013.01); *A61K 33/00* (2013.01); *A61M 11/005* (2013.01);
(Continued)

(58) Field of Classification Search
CPC .. C25B 9/23; C25B 1/04; C25B 15/08; C25B 9/19
See application file for complete search history.

(56) References Cited

U.S. PATENT DOCUMENTS 11,105,003 B2 * 8/2021 Lin .......................... C25B 9/73
2003/0215680 A1 11/2003 Lillis et al.
(Continued)

FOREIGN PATENT DOCUMENTS

AU 2018217248 A1 3/2019
CA 2915763 A1 2/2015
(Continued)

OTHER PUBLICATIONS

Examination Report dated Jan. 19, 2021 for AU application No. 2019204698.
(Continued)

*Primary Examiner* — Brian W Cohen
(74) *Attorney, Agent, or Firm* — Rosenberg, Klein & Lee

(57) ABSTRACT

An ion-exchange membrane electrolysis device includes an ion-exchange membrane electrolytic cell and an integrally formed integrated flow channel device. The ion-exchange membrane electrolytic cell generates a gas comprising hydrogen. The integrated flow channel device has a first setting structure, a water tank structure, a gas flow channel system and a water flow channel system. The water tank structure accommodates water. The first setting structure is configured for removably fixing the ion-exchange membrane electrolytic cell to the integrated flow channel device. The water flow channel system connects the water tank structure and the first setting structure for inputting the water in the water tank structure into the ion-exchange membrane electrolytic cell. The gas flow channel system is connected to the first setting structure for receiving and transporting the gas comprising hydrogen. Therefore, the present invention integrates functionally independent pathways, decreases pipeline connections, reduces volume of device, and improves safety of operation.

20 Claims, 18 Drawing Sheets

(51) Int. Cl.
*C25B 9/23* (2021.01)
*A61M 11/00* (2006.01)
*A61M 16/12* (2006.01)
*A61K 9/00* (2006.01)
*A61K 33/00* (2006.01)
*A61M 16/10* (2006.01)
*C25B 9/73* (2021.01)

(52) U.S. Cl.
CPC .......... *A61M 16/10* (2013.01); *A61M 16/125* (2014.02); *C25B 9/23* (2021.01); *C25B 9/73* (2021.01); *C25B 15/08* (2013.01); *A61M 2202/02* (2013.01)

(56) References Cited

U.S. PATENT DOCUMENTS

| | | |
|---|---|---|
| 2011/0132748 A1 | 6/2011 | Haryu et al. |
| 2012/0073525 A1* | 3/2012 | Owens ................ C01B 13/0207 123/3 |
| 2013/0108939 A1 | 5/2013 | Besse et al. |
| 2017/0327960 A1* | 11/2017 | Kurashina ............... C25B 15/02 |
| 2018/0057948 A1 | 3/2018 | Lin |
| 2018/0320275 A1 | 11/2018 | Lin |

FOREIGN PATENT DOCUMENTS

| | | |
|---|---|---|
| CA | 3014948 A1 | 2/2019 |
| CN | 106906483 A | 6/2017 |
| CN | 206872952 U | 1/2018 |
| EP | 3447168 A2 | 2/2019 |
| JP | H08239788 A | 9/1996 |
| JP | 2005523568 A | 8/2005 |
| RU | 153346 U1 | 7/2015 |
| SG | 10201807058X | 3/2019 |
| TW | 201723233 | 10/2016 |

OTHER PUBLICATIONS

Office Action dated Feb. 16, 2021 for CA application No. 3,048,418.
Office Action dated Jan. 15, 2021 for KR application No. 10-2019-0083424.
Office Action dated Aug. 21, 2020 for CA application 3,048,418.
Office Action dated Aug. 25, 2020 for IN application 201924026491.
Office Action dated Oct. 12, 2020 for RU application 2019121064/04(041214).
Notification of Reasons for Refusal dated Oct. 13, 2020 for JP application 2019-124254.

* cited by examiner

ION-EXCHANGE MEMBRANE ELECTROLYSIS DEVICE

The present application is based on, and claims priority from, China publication number CN108950588A, filed on 2018 Jul. 10, the disclosure of which is hereby incorporated by reference herein in its entirety.

BACKGROUND OF THE INVENTION

Field of the Invention

The present invention provides an ion-exchange membrane electrolysis device, and more particularly, to an ion-exchange membrane electrolysis device comprising an integrated flow channel device formed integrally for reducing volume, reducing connections of the tubes, and improving safety.

Description of the Prior Art

For long time, people have paid much attention on human life. Many medical technologies have been developed to fight disease and extend human life, but most medical treatments in the past are passive. That is to say, the disease is treated when it occurs, such as surgery, drug administration, chemotherapy and radiotherapy of the cancer, or nursery, rehabilitation, and correction of the chronic disease. However, in recent years, many medical experts have gradually made researches toward preventive medical methods, such as health food research, genetic disease screening, early prevention, etc., for actively preventing future morbidity. In addition, in order to extend human life, many anti-aging and anti-oxidation technologies have been developed and widely used by the public, including smear-care products and antioxidant foods/drugs.

Studies have found that the unstable oxygen (O+), also known as free radicals (harmful free radicals), produced by the human body for various reasons (such as disease, diet, environment or lifestyle) can be mixed with the inhaled hydrogen to form part of water and then get excreted so that the number of free radicals in the human body can be reduced to regain a healthy alkaline body from an acidic body, to resist oxidation and aging, to eliminate chronic disease, and to achieve beauty care effects. Clinical trials have shown that some long-term bedridden patients who have lung damage caused by long-term breathing high concentrations of oxygen can be relieved by inhaling hydrogen.

At present, hydrogen generators are gradually being used in medical places and homes. Large amount of highly standardized production will be an important goal for the hydrogen generators in the future. In addition, the hydrogen generator is composed of a plurality of functionally independent devices coupled to each other by pipes. However, in the prior art, the pipelines between devices need to be assembled separately, which causes cumbersome procedures, troublesome wiring assembly, high cost, difficulty in standardization, difficulty in shrinking the volume, and even the falling-off of the flow channel and water leaks in use.

SUMMARY OF THE INVENTION

In response to the above-mentioned problems, the present invention provides an integrated ion membrane electrolysis device, which integrates pipelines into an integrated flow channel device and has accommodation spaces for configuring corresponding devices. The devices with independent functions devices and the channels are integrated to avoid additional connections of tubes, reduce the volume of the ion-exchange membrane electrolysis device, greatly reduce the manufacturing cost, and improve the operational safety of the ion-exchange membrane electrolysis device.

An objective of the present invention is to provide an ion-exchange membrane electrolysis device, comprising an ion-exchange membrane electrolysis cell and an integrated flow channel device. The ion-exchange membrane electrolysis cell is configured to electrolyze water to produce a gas comprising hydrogen. The integrated flow channel device is integrally formed and includes a water tank structure, a plurality of setting structures, a water flow channel system and a gas flow channel system. The water tank structure is configured for accommodating water. A first setting structure of the plurality of setting structures is configured to set the ion-exchange membrane electrolysis cell therein and detachably fasten the ion-exchange membrane electrolysis cell to the integrated flow channel device. The water flow channel system is coupled to the first setting structure and the water tank structure to input the water from the water tank structure to the ion-exchange membrane electrolysis cell. The gas flow channel system is coupled to the first setting structure to receive the gas comprising hydrogen generated by the ion-exchange membrane electrolysis cell.

The first setting structure has a hydrogen input port, an oxygen input port and a water output port. The oxygen input port and the water output port are coupled to the water flow channel system and the water tank structure through the water flow channel system.

In an embodiment, the integrated flow channel device further comprises a second accommodating structure for accommodating a gas-water separator. The gas-water separator is coupled to the first setting structure through the gas flow channel system to receive the gas comprising hydrogen generated by the ion-exchange membrane electrolysis cell and retain liquid water of the gas comprising hydrogen, and then output the gas comprising hydrogen through a first flow channel of the gas flow channel system.

In another embodiment, the integrated flow channel device further comprises the second accommodating structure configured therein. The second accommodating structure is coupled to the hydrogen input port of the first setting structure through the gas flow channel system to receive the gas comprising hydrogen generated by the ion-exchange membrane electrolysis cell and retain liquid water of the gas comprising hydrogen, and then output the gas comprising hydrogen through a first flow channel of the gas flow channel system.

Wherein, a bobber is configured in the second accommodating structure. When the liquid water accommodated in the second accommodating structure reaches to a water level, the bobber blocks the gas comprising hydrogen from passing through the first flow channel of the gas flow channel system.

In addition, a spring valve is configured in the second accommodating structure. When the gas pressure of the gas comprising hydrogen in the second accommodating structure is equal to a pressure threshold, the spring valve is opened to connect the second accommodating structure and the gas flow channel system.

In an embodiment, the integrated flow channel device further comprises a third accommodating structure configured therein. The third accommodating structure is coupled to the first setting structure through the gas flow channel system. The ion-exchange membrane electrolysis device further comprises a filter detachably fastened in the third accommodating structure. The filter receives the gas comprising hydrogen through the gas flow channel system and outputs the filtered gas comprising hydrogen through a third flow channel of the gas flow channel system.

In an embodiment, the integrated flow channel device further comprises a fourth setting structure configured therein. The fourth setting structure is coupled with the first setting structure through the gas flow channel system. The ion-exchange membrane electrolysis device further includes a nebulizer detachably fastened in the fourth setting structure, whereby the nebulizer could extend into the water tank. The nebulizer receives the gas comprising hydrogen through the gas flow channel system. The nebulizer selectively generates an atomizing gas, and mixes the gas comprising hydrogen with the atomizing gas to be outputted.

Wherein, the nebulizer accommodates a liquid to be atomized, and the nebulizer including a cotton column and a microporous vibrating plate. One end of the cotton column is immersed in the liquid to be atomized to absorb the liquid to be atomized, and the microporous vibrating plate surrounds the other end of the cotton column to atomize the liquid to be atomized absorbed by the cotton column to generate the atomizing gas.

Also, the maximum atomization amount of the nebulizer is greater than or equal to 20 mL/hr.

In an embodiment, the integrated flow channel device further comprises a fifth accommodating structure located in the integrated flow channel device. The fifth accommodating structure is coupled to the first setting structure through the gas flow channel system. The ion-exchange membrane electrolysis device further includes a gas supplement fan detachably fastened to the fifth accommodating structure. The gas supplement fan is configured to introduce an external air from the outside of the ion-exchange membrane electrolysis device. The gas flow channel system receives the external air and mixes it with the gas comprising hydrogen to form a diluted gas comprising hydrogen.

Wherein, the above-mentioned setting structure respectively has a fitting structure including a fitting opening, a fitting hole, a fitting tube, a fitting cassette or a fitting clip.

Wherein, the ion-exchange membrane electrolysis cell has a first side and includes a hydrogen output tube coupled to the hydrogen input port, an oxygen output tube coupled to the oxygen input port, and a water input tube coupled to the water output port. The oxygen output tube and the hydrogen output tube respectively output a gas comprising oxygen to the oxygen input port and the gas comprising hydrogen to the hydrogen input port from the first side of the ion-exchange membrane electrolysis, and the water input tube receives water through the water output port from the first side.

The ion-exchange membrane electrolysis cell also generates the gas comprising oxygen with thermal energy when the water is electrolyzed. The integrated flow channel device further comprises a preheating sink structure coupled to the water flow channel system, and coupled to the water tank structure and the first setting structure through the water flow channel system. The preheating sink structure receives the water in the water tank structure, and replenishes the water through the water outlet port to the ion-exchange membrane electrolytic cell. The preheating sink structure receives the gas comprising oxygen with thermal energy through the oxygen input port.

Further, the water tank structure, the preheating sink structure, the setting structure, the gas flow channel system and the water flow channel system are integrally formed to form the integrated flow channel device.

Moreover, the position of the water tank structure is higher than that of the ion-exchange membrane electrolytic cell.

In an embodiment, the ion-exchange membrane electrolysis cell further comprises an operation panel. The operation panel is configured to adjust the flow rate of the gas comprising hydrogen to be outputted by the ion-exchange membrane electrolysis device in a range between 2 L/min and 6 L/min, wherein the concentration of the gas comprising hydrogen to be outputted is less than 4%, the volume of the ion-exchange membrane electrolysis device is less than 15 liters, and the maximum using power of the ion-exchange membrane electrolysis device is less than 240 W.

In another embodiment, the ion-exchange membrane electrolysis cell further comprises an operation panel. The operation panel is configured to adjust the flow rate of the gas comprising hydrogen to be outputted by the ion-exchange membrane electrolysis device in a range between 400 mL/min and 600 mL/min, wherein the concentration of the gas comprising hydrogen to be outputted is greater than 99%, the volume of the ion-exchange membrane electrolysis device is less than 13 liters, and the maximum using power of the ion-exchange membrane electrolysis device is less than 400 W.

As used herein, "coupled" or "connected" may include either direct or indirect communication.

In summary, the ion-exchange membrane electrolysis device of the present invention comprises the integrated flow channel device. The integrated flow channel device has the gas flow channel system, water flow channel system and a plurality of setting structures. The gas flow channel system is configured to transport hydrogen from the ion-exchange membrane electrolysis device to each device in each setting structure, such as the ion-exchange membrane electrolysis cell, the filter, the nebulizer and the gas supplement fan. The water flow channel system is configured to couple the water tank structure with the ion-exchange membrane electrolysis cell. The design of the gas flow channel system and the water flow channel system replaces the additional piping to simplify the piping in the production process and reduces pipe consumables and labor costs. The arrangement of the reserved space facilitates the attachment of other devices to the integrated flow channel device, such as the ion-exchange membrane electrolysis cell, the filter, the nebulizer and the gas supplement fan, so that the devices could be stably disposed in the ion-exchange membrane electrolysis device. More importantly, the integrated flow channel device integrates the complicated pipelines of the ion-exchange membrane electrolysis device, reduces the reserved space for the pipes required in the ion-exchange membrane electrolysis device, optimizes space utilization, and reduces the possibility of water leaking and gas leaking to improve operational safety of the ion-exchange membrane electrolysis device.

BRIEF DESCRIPTION OF THE APPENDED DRAWINGS

Some of the embodiments will be described in detail, with reference to the following figures, wherein like designations denote like members, wherein.

The advantages, spirits, and features of the present invention will be explained and discussed with embodiments and figures as follows.

DETAILED DESCRIPTION OF THE INVENTION

A detailed description of the hereinafter described embodiments of the disclosed apparatus and method are presented herein by way of exemplification and not limitation with reference to the Figures. Although certain embodiments are shown and described in detail, it should be understood that various changes and modifications can be made without departing from the scope of the appended claims. The scope of the present invention will in no way be limited to the number of constituting components, the materials thereof, the shapes thereof, the relative arrangement thereof, etc., and are disclosed simply as an example of embodiments of the present invention.

In the description of the present specification, the terminologies "in an embodiment", "in another embodiment", or "in some embodiments" means that the specific feature, structure, material or characteristic of the present embodiment is involved in at least one embodiment of the present invention. In the description of the present specification, the schematic representation of the mentioned terminologies does not necessarily refer to the same embodiment. Furthermore, the described specific feature, structure, material or characteristic can be involved in any one or more embodiments in a proper way.

In the embodiments of the present specification, the terminology "or" includes the combination of part of listed components, and the combination of all the listed components. For example, the described "A or B" includes only A, only B, and both A and B. Moreover, the terminologies "a" and "the" before the element or component of the present invention do not limit the number of element or component. Therefore, the terminologies "a" and "the" should be read as including one or at least one. Besides, the singular form of element or component also includes the plural form, unless the number clearly refers to the singular form.

Figure 1A:
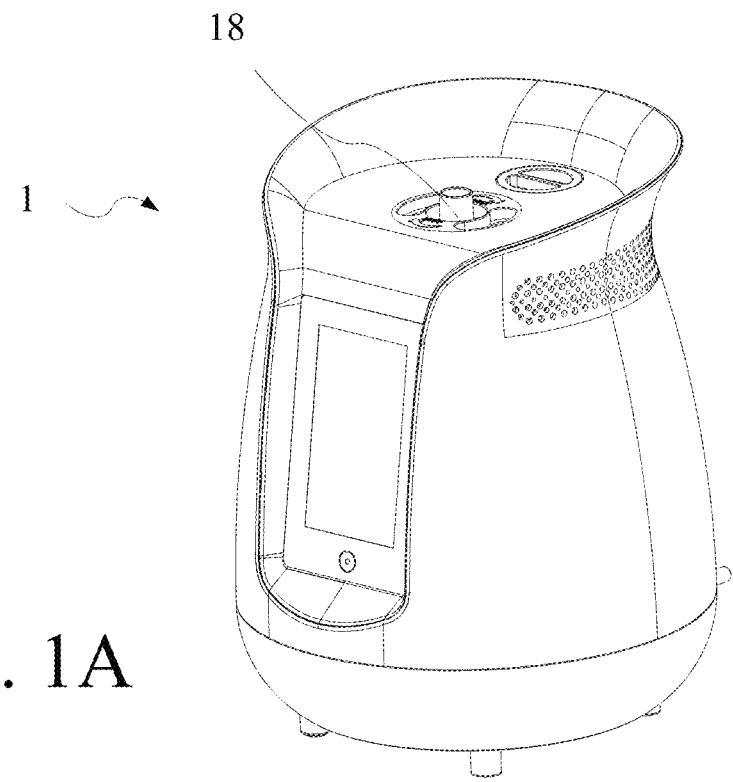
FIG. 1A and FIG. 1B are the appearance diagrams illustrating the ion-exchange membrane electrolysis devices according to different embodiments of the present invention.
Figure 1B:
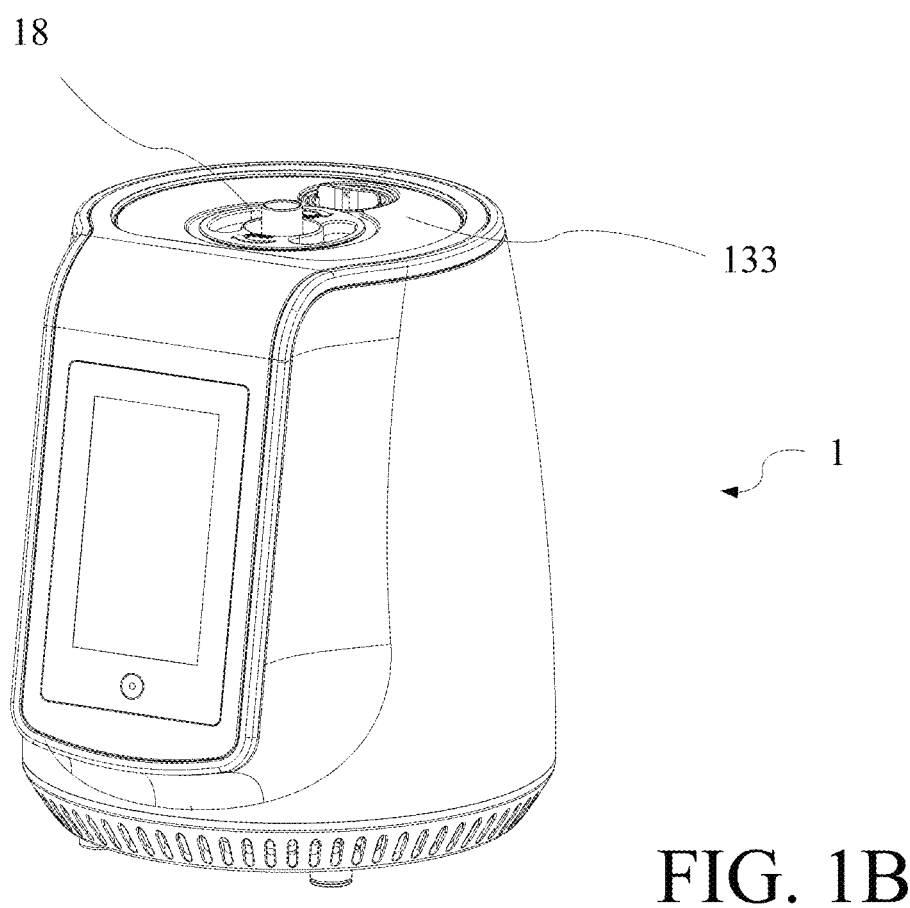
Figure 2:
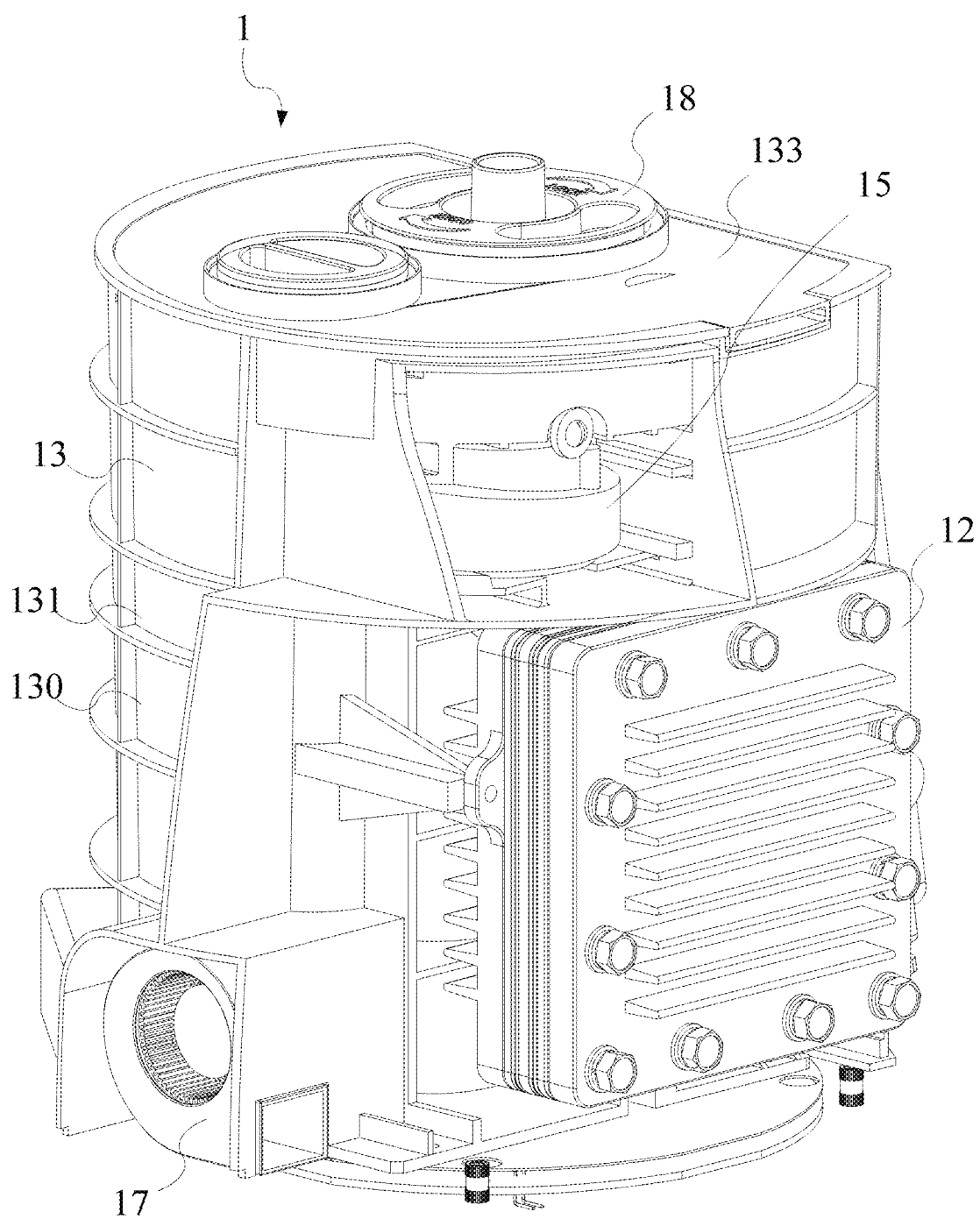
FIG. 2 is a schematic diagram illustrating the ion-exchange membrane electrolysis device removing the outer casing according to an embodiment of the present invention.
Figure 3A:
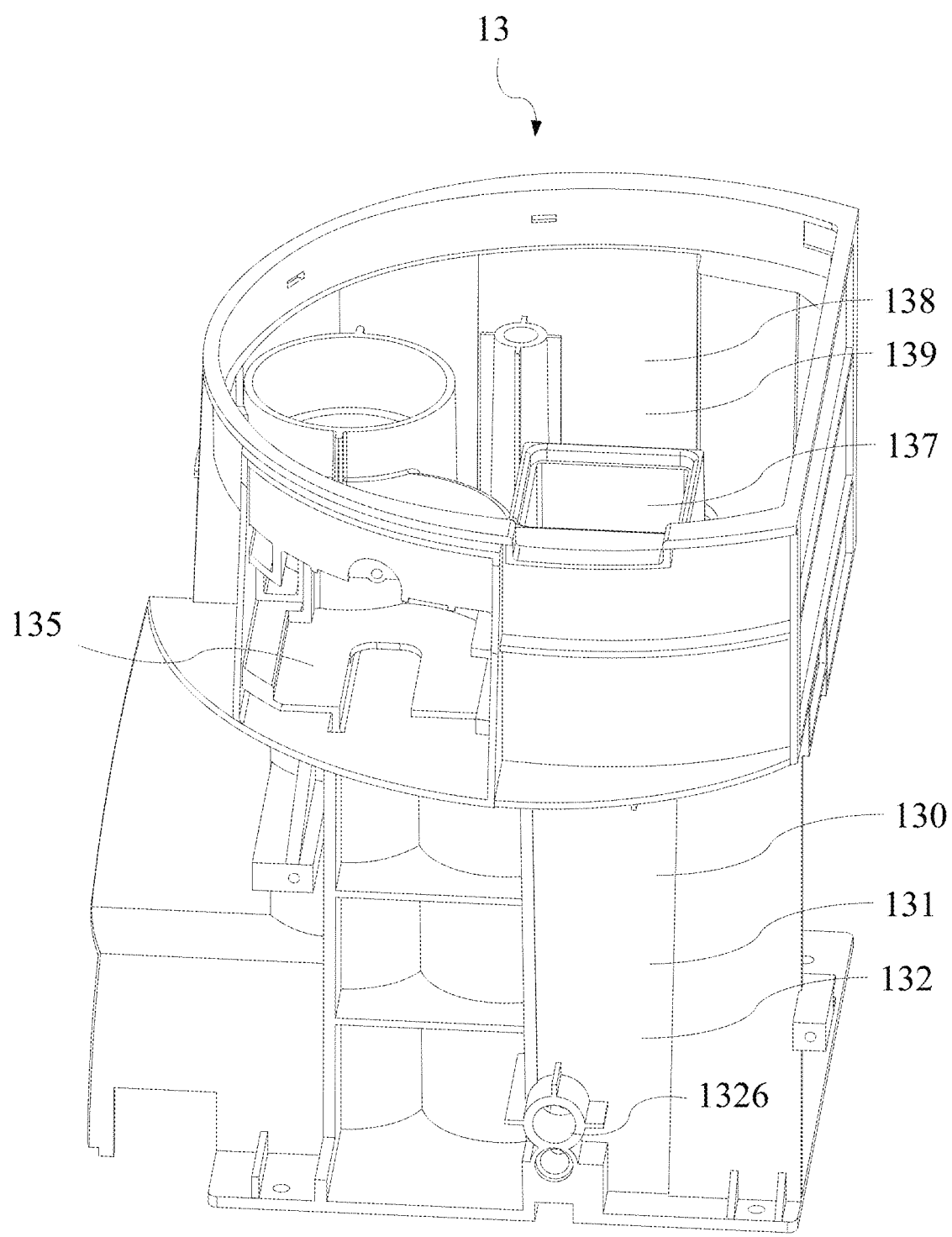
FIG. 3A and FIG. 3B are the schematic diagrams illustrating the integrated flow channel devices according to different embodiments of the present invention.
Figure 3B:
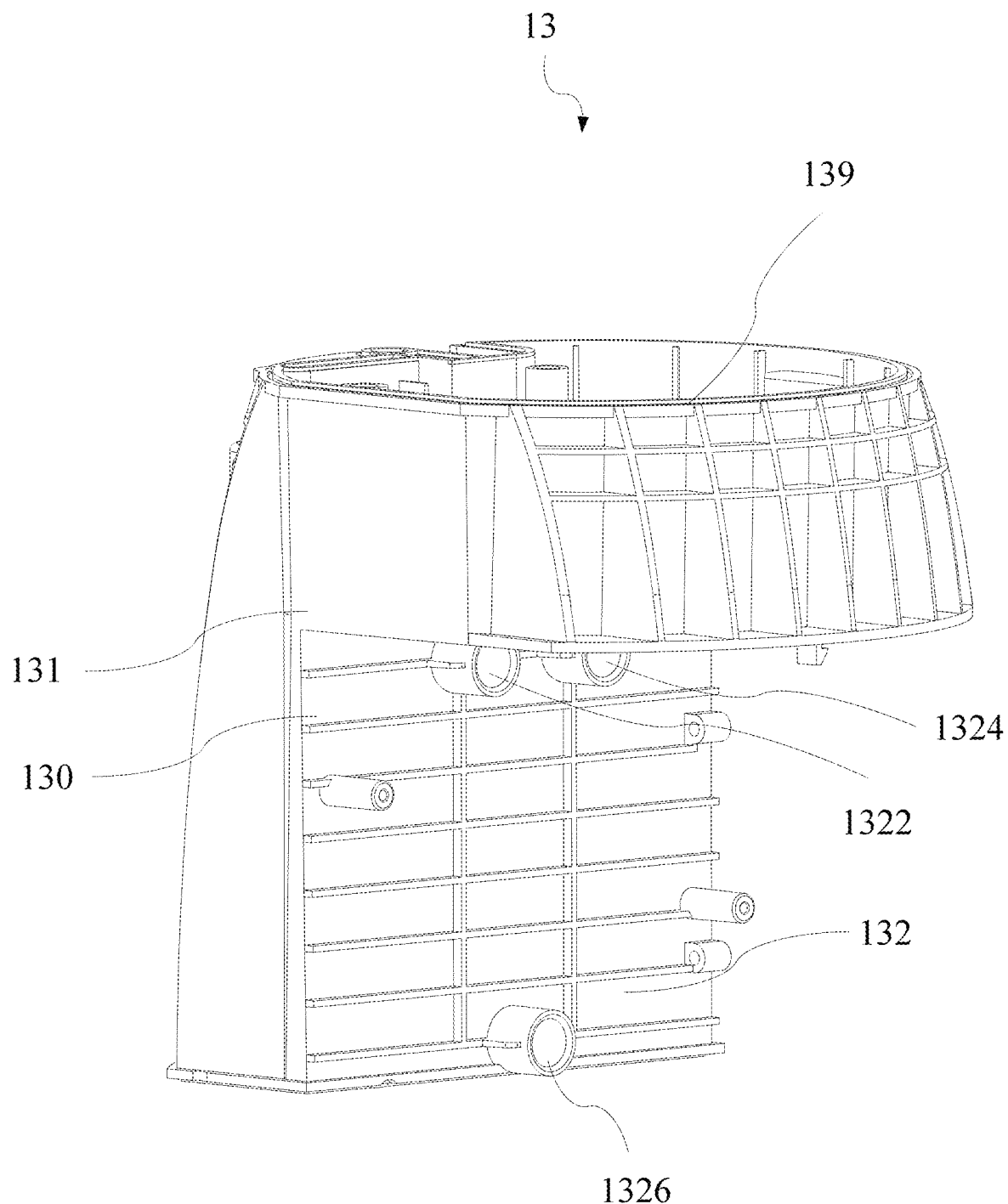

Please refer to FIG. 1A to FIG. 3B. FIG. 1A and FIG. 1B are the appearance diagrams illustrating the ion-exchange membrane electrolysis devices according to different embodiments of the present invention. FIG. 2 is a schematic diagram illustrating the ion-exchange membrane electrolysis device removing the outer casing according to an embodiment of the present invention. FIG. 3A and FIG. 3B are the schematic diagrams illustrating the integrated flow channel devices according to different embodiments of the present invention. As shown in FIG. 1A to FIG. 3B, the present invention is providing an ion-exchange membrane electrolysis device 1, comprising an ion-exchange membrane electrolysis cell 12 and an integrated flow channel device 13. The ion-exchange membrane electrolysis cell 12 is configured to electrolyze water to produce a gas comprising hydrogen. The integrated flow channel device 13 is integrally formed and includes a water tank structure 139, a plurality of setting structures, a gas flow channel system 130 and a water flow channel system 131. The water tank structure 139 is configured for accommodating water. A first setting structure 132 of the plurality of setting structures is configured to detachably fastening the ion-exchange membrane electrolysis cell 12 therein. The water flow channel system 131 includes a plurality of flow channels coupling the water tank structure 139 to input water from the water tank structure 139 to the ion-exchange membrane electrolysis cell 12. The gas flow channel system 130 includes a plurality of flow channels respectively coupled to the plurality of setting structures, and receives the gas comprising hydrogen through the flow channels and respectively transport the gas comprising hydrogen to the plurality of setting structures. The first setting structure 132 has a hydrogen input port 1322, an oxygen input port 1324 and a water output port 1326. The water tank structure 139 is coupled to the water output port 1326 by the water flow channel system 131 to input water in the water tank structure 139 to the ion-exchange membrane electrolysis cell 12, and the gas flow channel system 130 receives the gas comprising hydrogen generated by the ion-exchange membrane electrolysis cell 12 through the hydrogen input port 1322.

The ion-exchange membrane electrolysis device 1 of the present invention fixes each of the devices therein by prearranged setting structures of the integrated flow channel device 13, so that the spatial structure of the ion-exchange membrane electrolysis device 1 is more clear during assembling. At the same time, gas and liquid are transported through the plurality of prearranged flow channels among the setting structures, without additional piping between two devices. Moreover, the plurality of flow channels are merged into a water flow channel system and a gas flow channel system to integrate functionally independent or related pipelines, thereby reducing hose or wire-like pipelines to avoid entanglement or misconnection of the pipelines. In addition, the cost of piping could be saved, and the danger of hidden pipelines falling out in the prior art could be avoided, thereby reducing the possibility of water leakage or air leakage. More importantly, each functionally independent device is integrated through the integrated flow channel device 13 to optimize space utilization.

Figure 4:
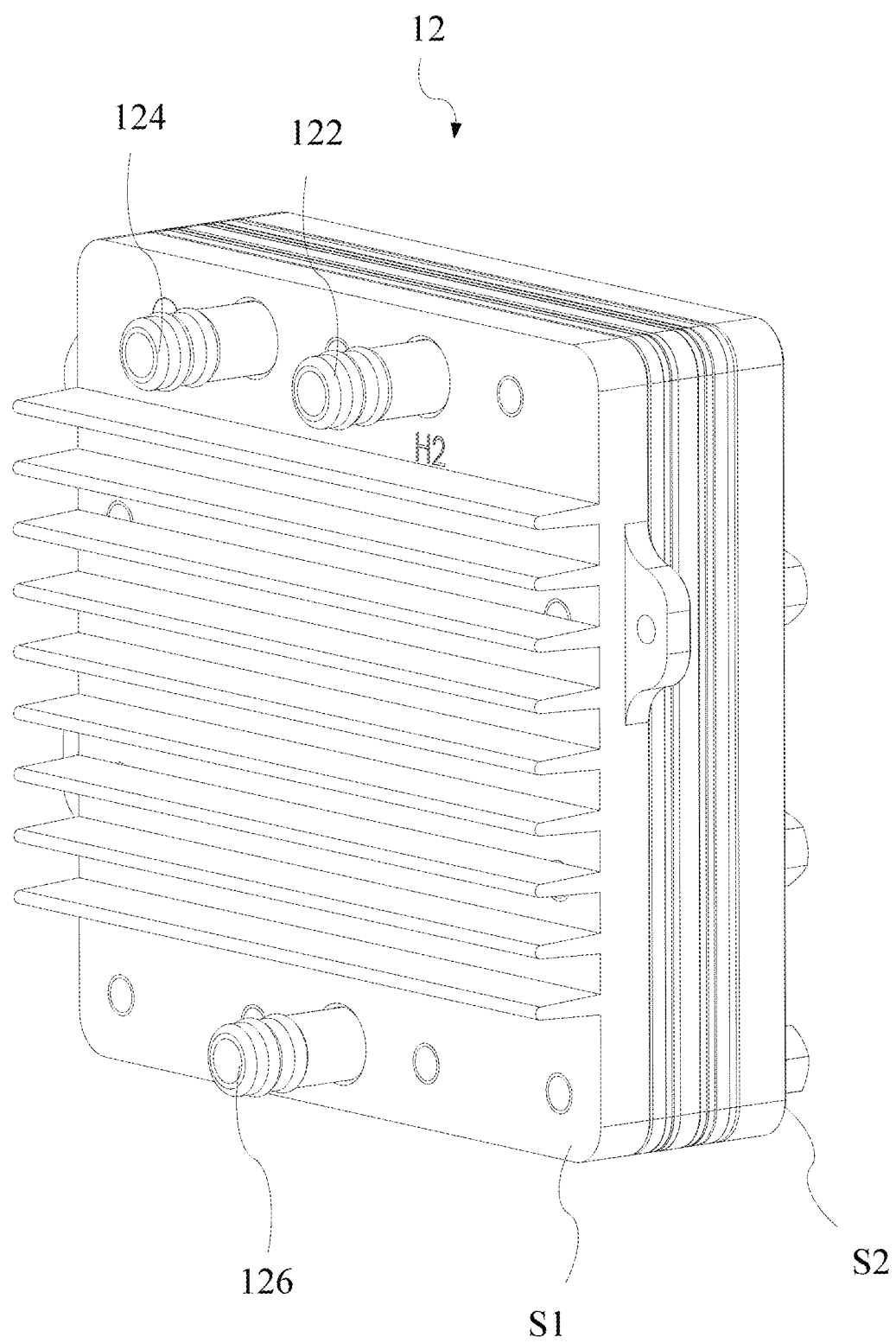
FIG. 4 is a schematic diagram illustrating the ion-exchange membrane electrolytic cell according to an embodiment of the present invention.
Figure 5:
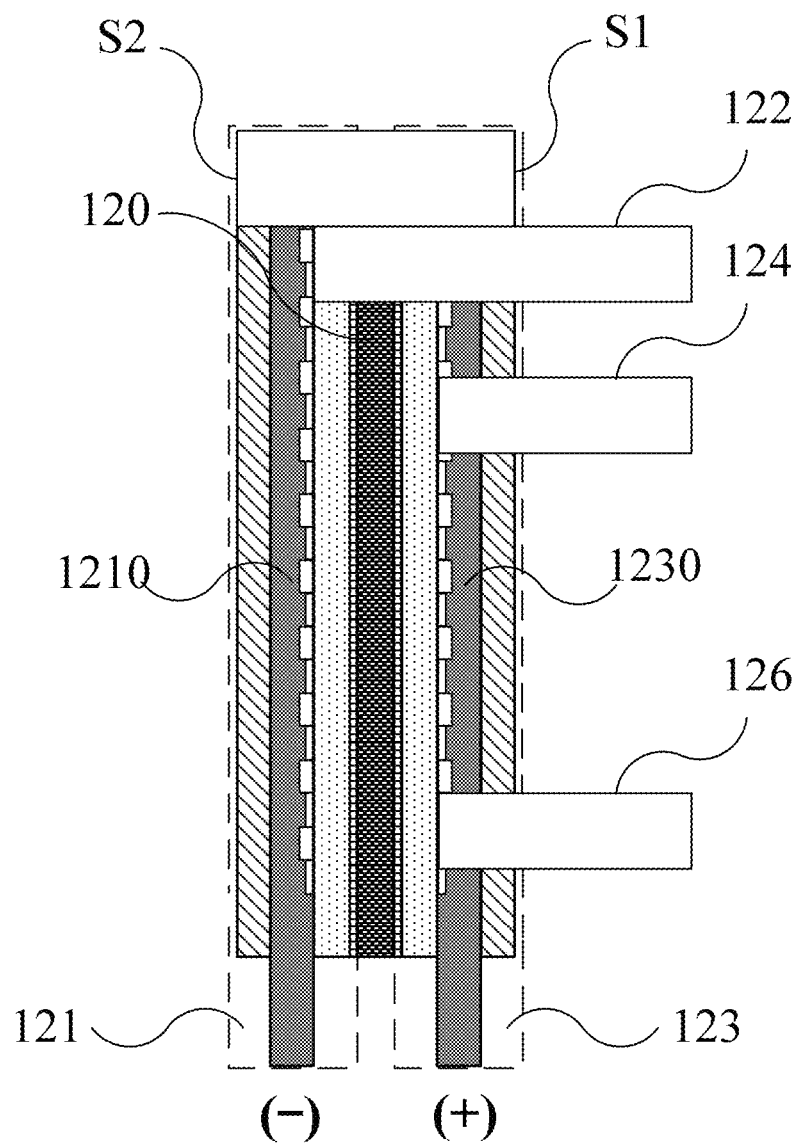
FIG. 5 is a cross-sectional diagram illustrating the ion-exchange membrane electrolytic cell according to an embodiment of the present invention.

Please refer to FIG. 4 and FIG. 5. FIG. 4 is a schematic diagram illustrating the ion-exchange membrane electrolytic cell 12 according to an embodiment of the present invention. FIG. 5 is a cross-sectional diagram illustrating the ion-exchange membrane electrolytic cell 12 according to an embodiment of the present invention. The ion-exchange membrane electrolytic cell 12 has a first side S1, a hydrogen output tube 122, an oxygen output tube 124 and a water input tube 126, wherein the hydrogen output tube 122, the oxygen output tube 124 and the water input tube 126 are located on the first side S1, and respectively coupled to an oxygen input port, a hydrogen input port and a water output port of the first setting structure 132. The oxygen output tube 124 and the hydrogen output tube 122 respectively output the gas comprising oxygen and the gas comprising hydrogen from the ion-exchange membrane electrolytic cell 12 of the first side S1 to the oxygen input port and hydrogen input port, and then the gas comprising oxygen and the gas comprising hydrogen respectively enter the gas flow channel system 130 and water flow channel system 131 through the oxygen input port and the hydrogen input port, wherein the oxygen input port is coupled with the water tank structure 139. The water input tube 126 of the ion-exchange membrane electrolytic cell 12 is coupled with the water output port of the water tank structure 139 from the first side S1 to input water. The directions of the oxygen output tube 124, the hydrogen output tube 122 and the water input tube 126 are not limited to the first side S1 (as in the direction of the anode of the embodiment), and may also be output from a second side S2 (as in the direction of the cathode of the embodiment) at the same time.

As shown in FIG. 5, the ion-exchange membrane electrolytic cell 12 includes an ion-exchange membrane 120, a cathode chamber 121 and an anode chamber 123. The cathode chamber 121 includes a cathode electrode 1210, the anode chamber 123 includes an anode electrode 1230, and the ion-exchange membrane 120 is disposed between the cathode chamber 123 and the anode chamber 123. When the ion-exchange membrane electrolytic cell 12 electrolyzes water, the cathode electrode 1210 generates hydrogen gas and the anode electrode 1230 generates oxygen gas. In an embodiment, the anode chamber 123 accommodates water, and the water in the anode chamber 123 may further pass through the ion-exchange membrane 120 to enter the cathode chamber 121. In addition, FIG. 5 is a cross-sectional schematic diagram only for explaining the internal structure of the ion-exchange membrane electrolytic cell 12 but not an actual internal structure diagram of the ion-exchange membrane electrolytic cell 12. The region where the second side S2 and the cathode electrode 1210 are located is called the cathode chamber 121, and the region where the first side S1 and the anode electrode 1230 are located is called the anode chamber 123. In order to more clearly express the corresponding positions of the cathode chamber 121 and the anode chamber 123, the position thereof is indicated by a dotted line in figures.

Figure 6:
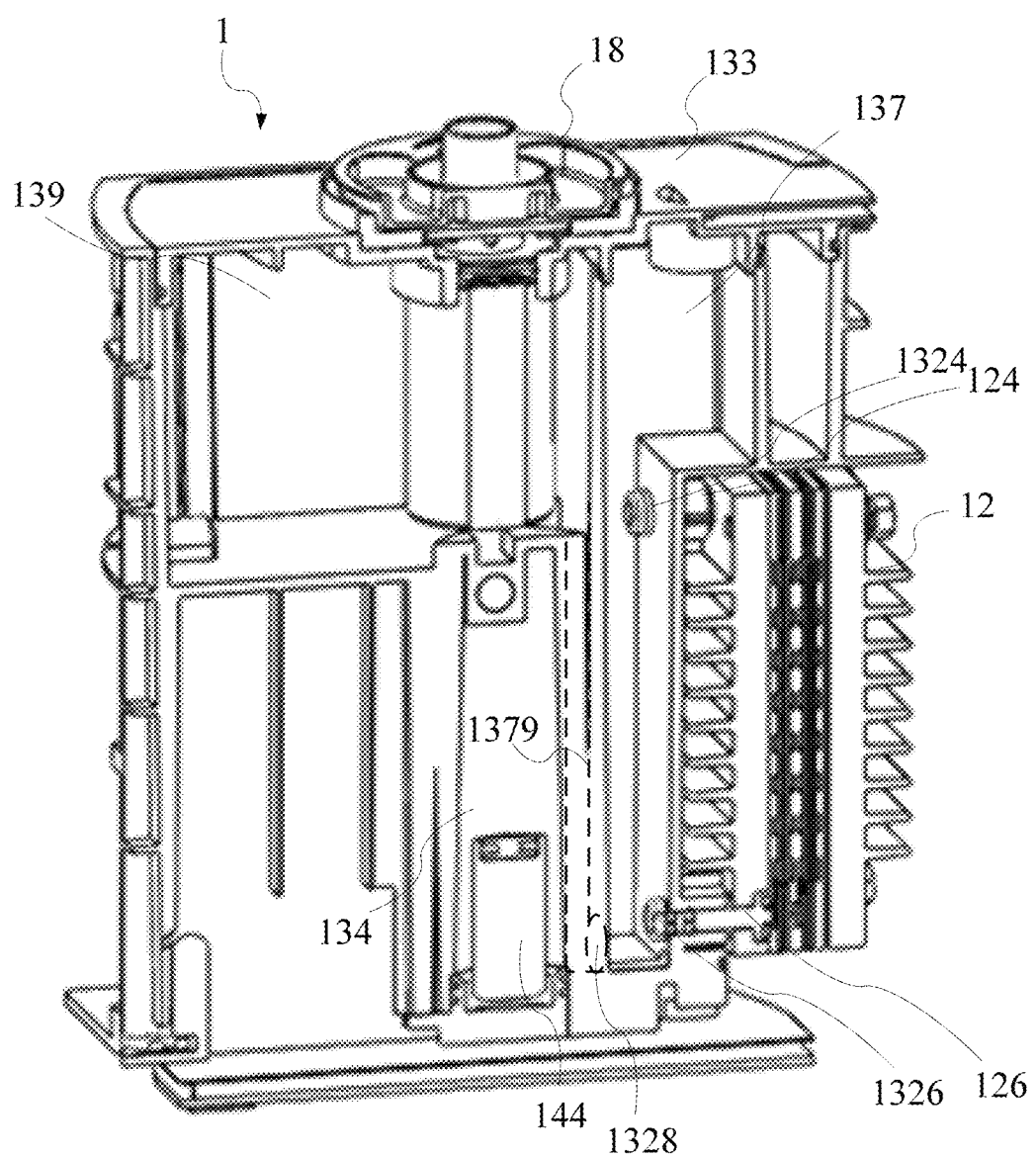
FIG. 6 is a cross-sectional diagram illustrating the ion-exchange membrane electrolysis device according to FIG. 2.
Figure 7:
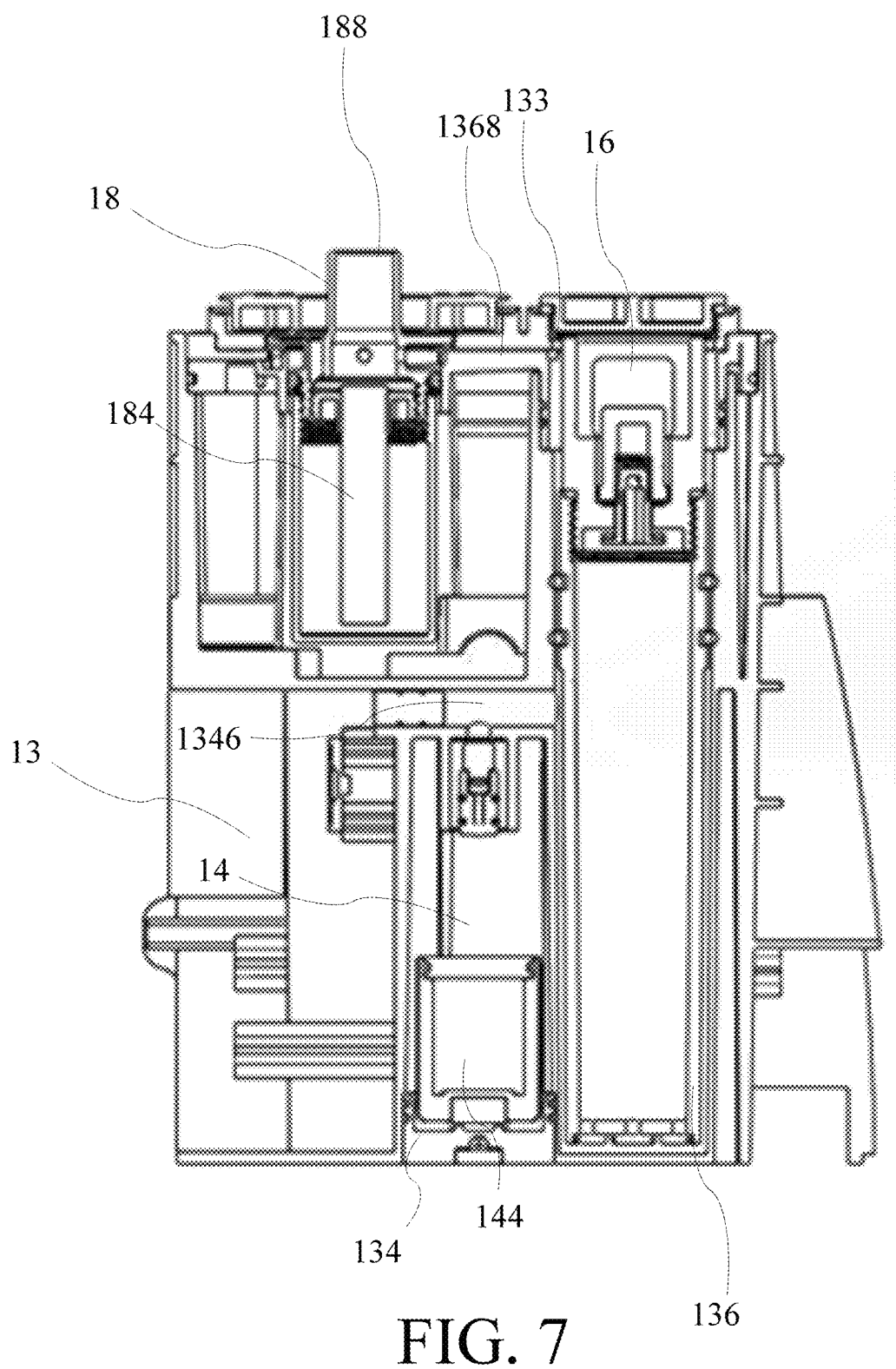
FIG. 7 is a cross-sectional diagram illustrating another view of the ion-exchange membrane electrolysis device according to FIG. 6.
Figure 9A:
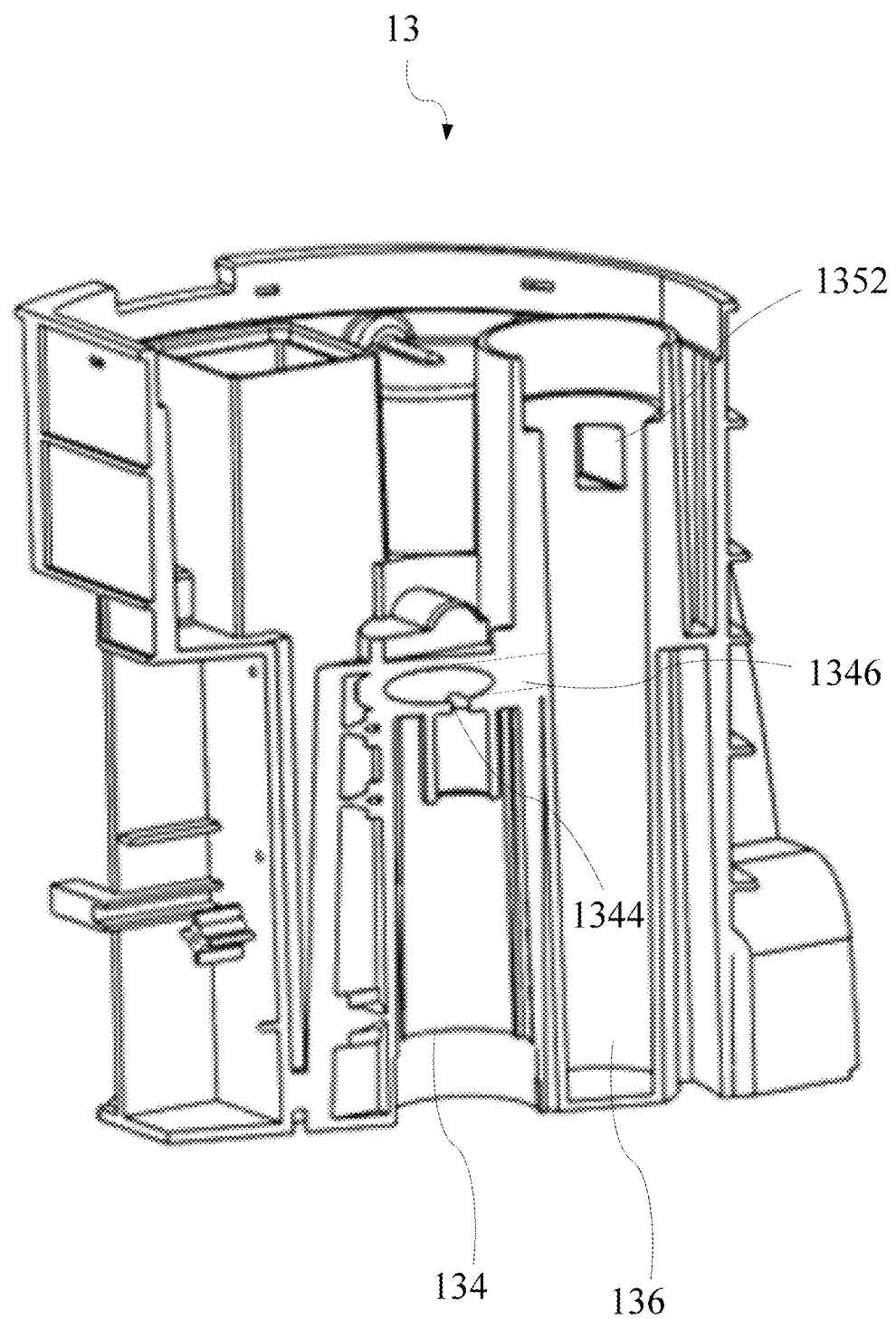
FIG. 9A and FIG. 9B are the cross-sectional diagrams illustrating the integrated flow channel devices according to different embodiments of the present invention.
Figure 9B:
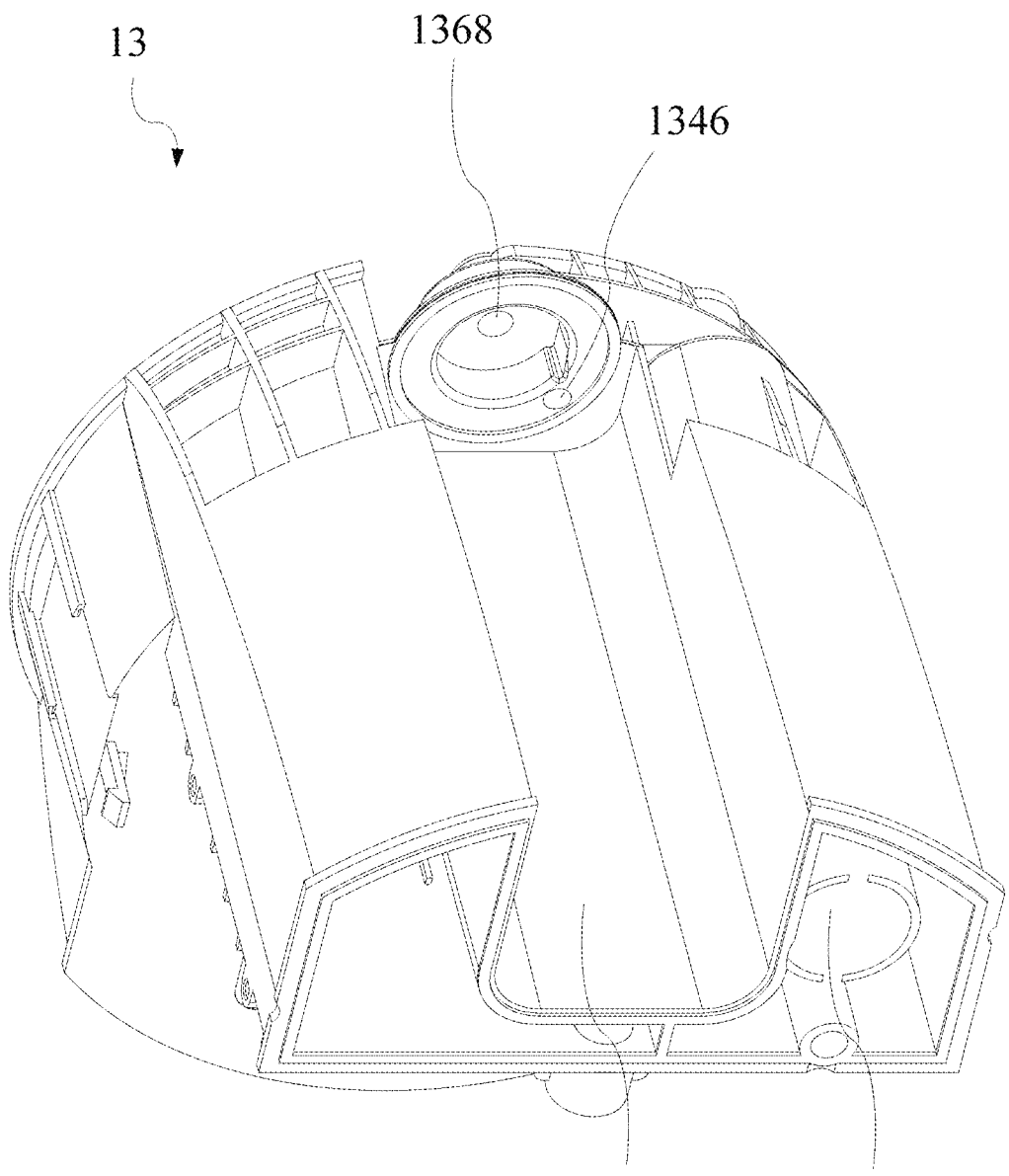
Figure 11:
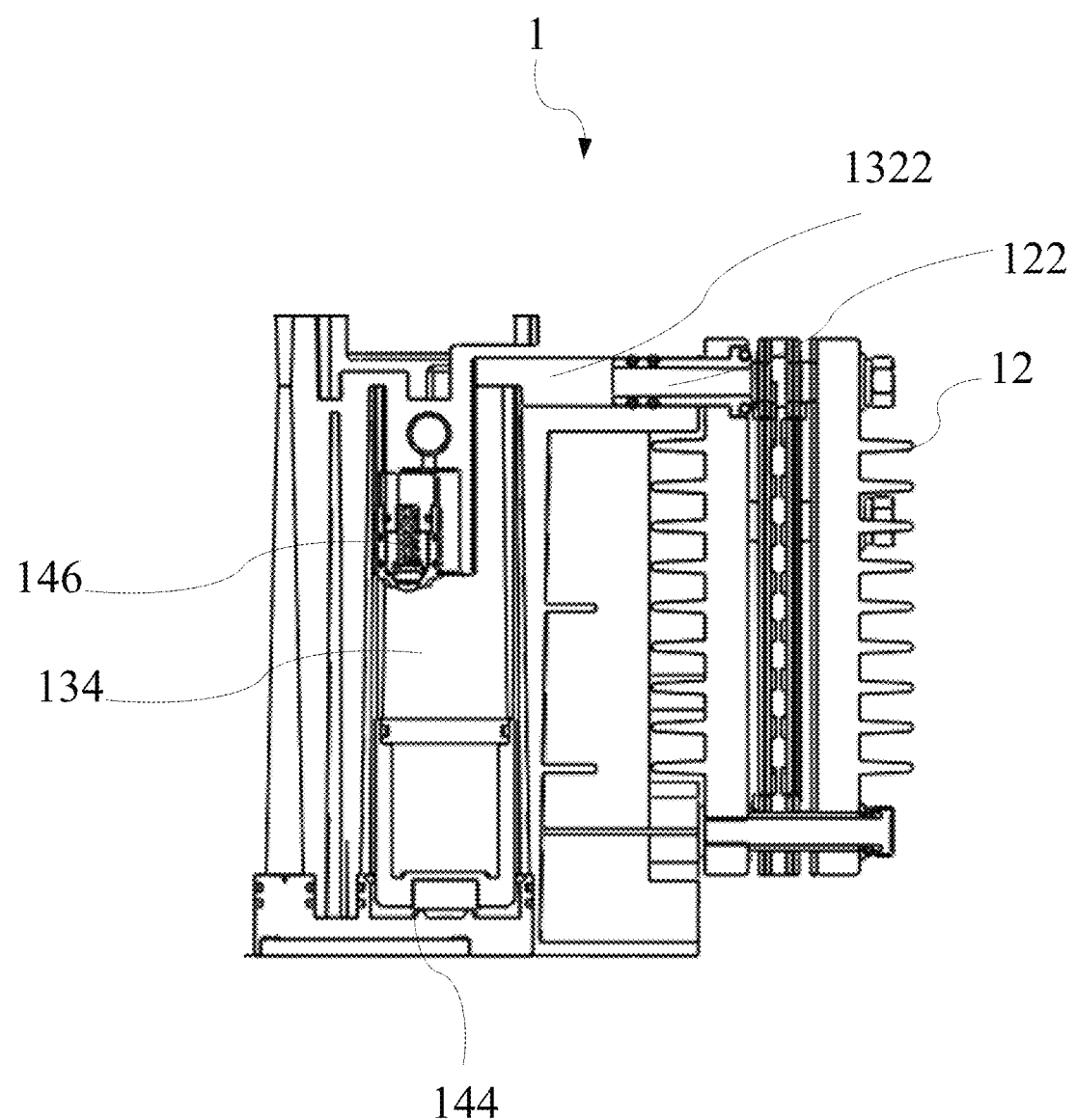
FIG. 11 is a partial cross-sectional diagram illustrating another section depth of the ion-exchange membrane electrolysis device according to FIG. 6.

Please refer to FIG. 6, FIG. 7, FIG. 9A, FIG. 9B and FIG. 11. FIG. 6 is a cross-sectional diagram illustrating the ion-exchange membrane electrolysis device 1 according to FIG. 2. FIG. 7 is a cross-sectional diagram illustrating another view of the ion-exchange membrane electrolysis device 1 according to FIG. 6. FIG. 9A and FIG. 9B are the cross-sectional diagrams illustrating different embodiments of the integrated flow channel devices 13 according to different embodiments of the present invention. FIG. 11 is a partial cross-sectional diagram illustrating another section depth of the ion-exchange membrane electrolysis device 1 according to FIG. 6. In an embodiment, the integrated flow channel device 13 further has a second accommodating structure 134 located therein. The second accommodating structure 134 is coupled to the first setting structure 132 through the gas flow channel system 130 for receiving the gas comprising hydrogen generated by the ion-exchange membrane electrolytic cell 12, retaining liquid water of the gas comprising the hydrogen, and then outputting the gas comprising hydrogen through a first flow channel 1346 of the gas flow channel system 130.

The second accommodating structure 134 communicates with hydrogen output tube 122 through the hydrogen input port 1322 of the gas flow channel system 130 to receive the gas comprising hydrogen generated by the ion-exchange membrane electrolytic cell 12. Since the temperature in the second accommodating structure 134 is lower than the temperature in the ion-exchange membrane electrolytic cell 12, the moisture in the gas comprising hydrogen is easily condensed into the liquid water in the second accommodating structure 134. The liquid water slides down and remains in the bottom space of the second accommodating structure 134, and the separated gas comprising hydrogen is output to a third accommodating structure 136 through the first flow channel 1346 of the gas flow channel system 130. The first flow channel 1346 could be disposed at an upper end of the second accommodating structure 134 to prevent the liquid water from flowing into the first flow channel 1346. Therefore, the second accommodating structure 134 could separate gas and liquid.

In an embodiment, the second accommodating structure 134 accommodates a bobber 144. The bobber 144 rises as the liquid water is accommodated in the second accommodating structure 134. When the liquid water accommodated in the second accommodating structure 134 reaches to a water level, the bobber 144 blocks the second accommodating structure 134 from communicating with an output port 1344 of the first flow channel 1346 to block the gas comprising hydrogen from passing through the first flow channel 1346. In practical applications, the bobber 144 can be a plastic hollow column to be raised by water. In addition, the second accommodating structure 134 has a flow channel port at the bottom of the second accommodating structure 134. The flow channel port is configured to allow the liquid water accommodated by the second accommodating structure 134 to flow to the outside of the ion-exchange membrane electrolysis device 1. When the water level in the second accommodating structure 134 is low, the bobber 144 does not float and block the flow channel port to prevent the external air from flowing into the second accommodating structure 134 through the flow channel port and prevent the gas comprising hydrogen from outputting from the ion-exchange membrane electrolysis device 1 through the flow channel port.

In another embodiment, the second accommodating structure 134 accommodates a spring valve 146 disposed on an output port 1344 of the integrated flow channel device 13.

The second accommodating structure 134 is connected to the first flow channel 1346 through the output port 1344. If the gas pressure does not reach to a pressure threshold, the spring valve 146 blocks the gas in the second accommodating structure 134 from passing through the output port 1344 into the first flow channel 1346. When the gas pressure of the gas comprising hydrogen in the second accommodating structure 134 reaches to the pressure threshold, the spring valve 146 is opened by the gas comprising hydrogen. Thereby, the spring valve 146 is opened to connect the second accommodating structure 134 and the first flow channel 1346, so that the gas comprising hydrogen could enter the first flow channel 1346. Wherein, the pressure threshold is greater than the ambient gas pressure and greater than the gas pressure in the first flow channel 1346. By the configuration of the spring valve 146, the time during which the gas comprising hydrogen remains in a gas-water separator 14 could be prolonged, and the efficiency of the separation of gas and water could be increased. Furthermore, it could prevent the external air from reversely entering into the second accommodating structure 134 along with the first flow channel 1346 after being drawn into the integrated flow channel device 13 by a gas supplement fan 15.

In the above embodiment, the function of separating gas and water is achieved by the design of the second accommodating structure 134 for accommodating the bobber 134 and the spring valve 146. However, the second accommodating structure 134 could also directly accommodate the device with function of separating gas and water. In another embodiment, the integrated flow channel device 13 further includes the second accommodating structure 134 for accommodating the gas-water separator 14. The gas-water separator 14 communicates with the first setting structure 132 through the gas flow channel system 130 to receive the gas comprising hydrogen generated by ion-exchange membrane electrolytic cell 12 and retain the liquid water of the gas comprising hydrogen, and then output the gas comprising hydrogen through the first flow channel 1346 of the gas flow channel system 130. The function of the gas-water separator 14 is the same as the function of the second accommodating structure 134. Namely, the gas-water separator 14 of the present invention could also be installed in the second accommodating structure 134 to execute the function of separating gas and water of the second accommodating structure 134 in the foregoing embodiment. In the specification of the present invention, the use of the gas-water separator 14 and the second accommodating structure 134 could be easily exchanged in a reasonable manner. On the other hand, by integrating the integrated flow channel device 13 including the hydrogen input port 1322, the output hole 1344, the first flow channel 1346, the water tank structure 139, and the plurality of setting structures, the devices could be connected to each other without additional pipelines.

Figure 10:
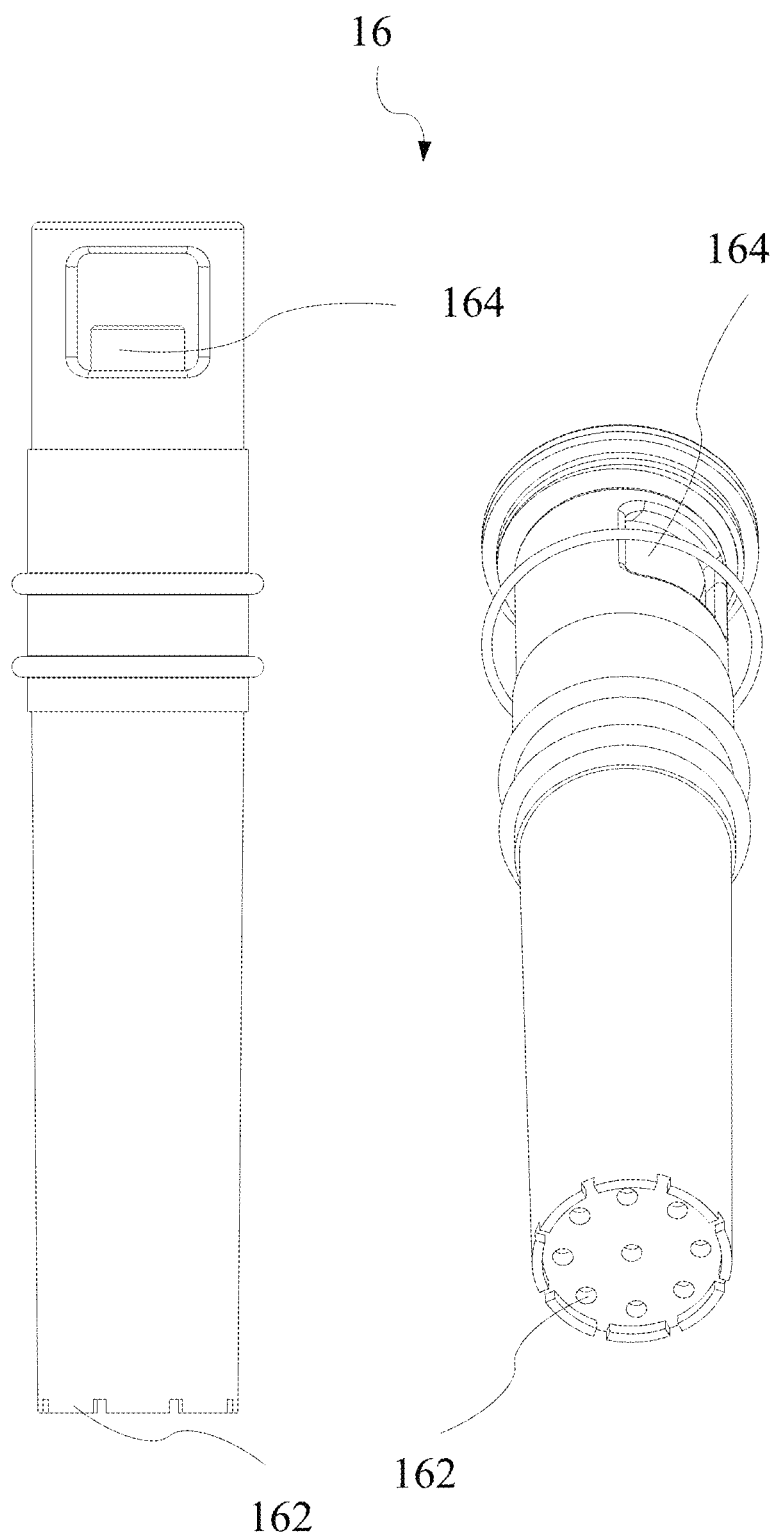
FIG. 10 is a schematic diagram illustrating another view of the filter according to an embodiment of the present invention.

Please refer to FIG. 7, FIG. 9A, FIG. 9B and FIG. 10. FIG. 10 is a schematic diagram illustrating another view of the filter 16 according to an embodiment of the present invention. In an embodiment, the integrated flow channel device 13 further comprises a third accommodating structure 136. The third accommodating structure 136 is coupled to the first setting structure 132 and the second accommodating structure 134 through the gas flow channel system 130. The ion-exchange membrane electrolysis device 1 further comprises a filter 16 detachably fastened in the third accommodating structure 136. The filter 16 receives the gas comprising hydrogen through the gas flow channel system 130 and outputs the filtered gas comprising hydrogen through the gas flow channel system 130. A filter input port 162 configured on the lower part of the filter 16 receives the gas comprising hydrogen from the first flow channel 1346 of the integrated flow channel device 13. The gas comprising hydrogen unidirectionally passes through the inner filter of the filter 16 and is filtered, and then the filtered gas comprising hydrogen is transported to a nebulizer 18 from the upper of thea filter output port 164.

The filtered gas comprising hydrogen is transported to the nebulizer 18 via communicating with a third flow channel 1368 of the gas flow channel system 130. In an embodiment, the integrated flow channel device 13 of the ion-exchange membrane electrolysis device 1 further includes an upper cover 133 disposed thereon. In some embodiments, the third flow channel 1368 can also be a portion of the upper cover 133.

Figure 12:
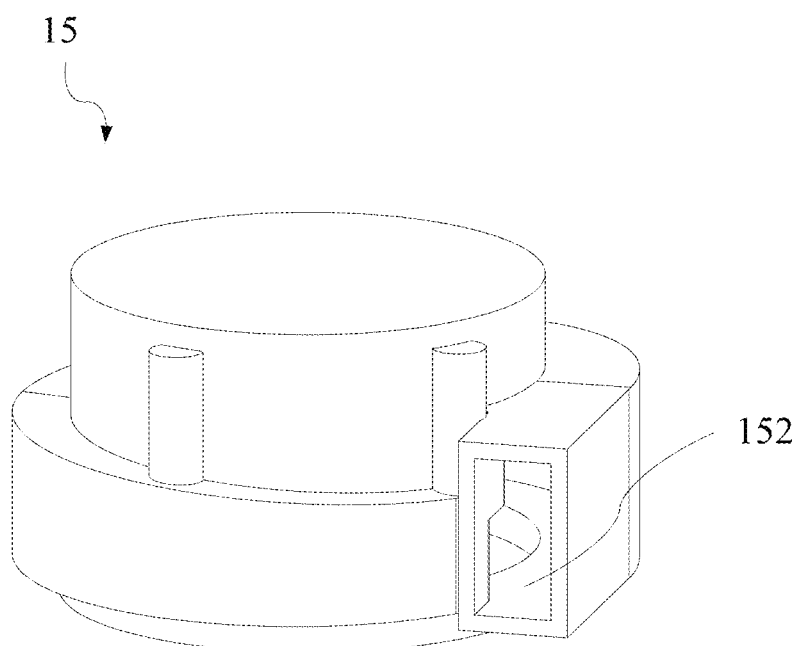
FIG. 12 is a schematic diagram illustrating the gas supplement fan according to an embodiment of the present invention.

Please refer to FIG. 2, FIG. 9A and FIG. 12. FIG. 12 is a schematic diagram illustrating the gas supplement fan 15 according to an embodiment of the present invention. In an embodiment, the integrated flow channel device 13 further comprises a fifth accommodating structure 135 located in the integrated flow channel device 13. The fifth accommodating structure 135 is connected to the first setting structure 132, the second accommodating structure 134 and the third accommodating structure 136 through the gas flow channel system 130. The ion-exchange membrane electrolysis device 1 further includes the gas supplement fan 15 detachably fastened to the fifth accommodating structure 135. The gas supplement fan 15 is configured to introduce an external air from the outside of the ion-exchange membrane electrolysis device 1, and input the external air from a gas supplement fan port of the gas supplement fan 15 into a second flow channel 1352. In an embodiment, the second flow channel 1352 leads to the third accommodating structure 136, so that the third accommodating structure 136 receives the external air and the external air enters into the filter 16 after mixing with the gas comprising hydrogen so as to output a diluted gas comprising hydrogen after filtering. In another embodiment, the second flow channel 1352 leads to the third flow channel 1368, and the external air mixes with the gas comprising hydrogen to form a diluted gas comprising hydrogen after filtering. In the above two embodiments, the concentration of hydrogen of the diluted gas comprising hydrogen could be adjusted to 4%, which is suitable for human begins to inhale.

By integrating the integrated flow channel device 13 including the first flow channel 1346 and the second flow channel 1352, the third accommodating structure 136, the second accommodating structure 134, the filter 16 and the gas supplement fan 15 are connected to each other without additional pipelines.

Figure 8:
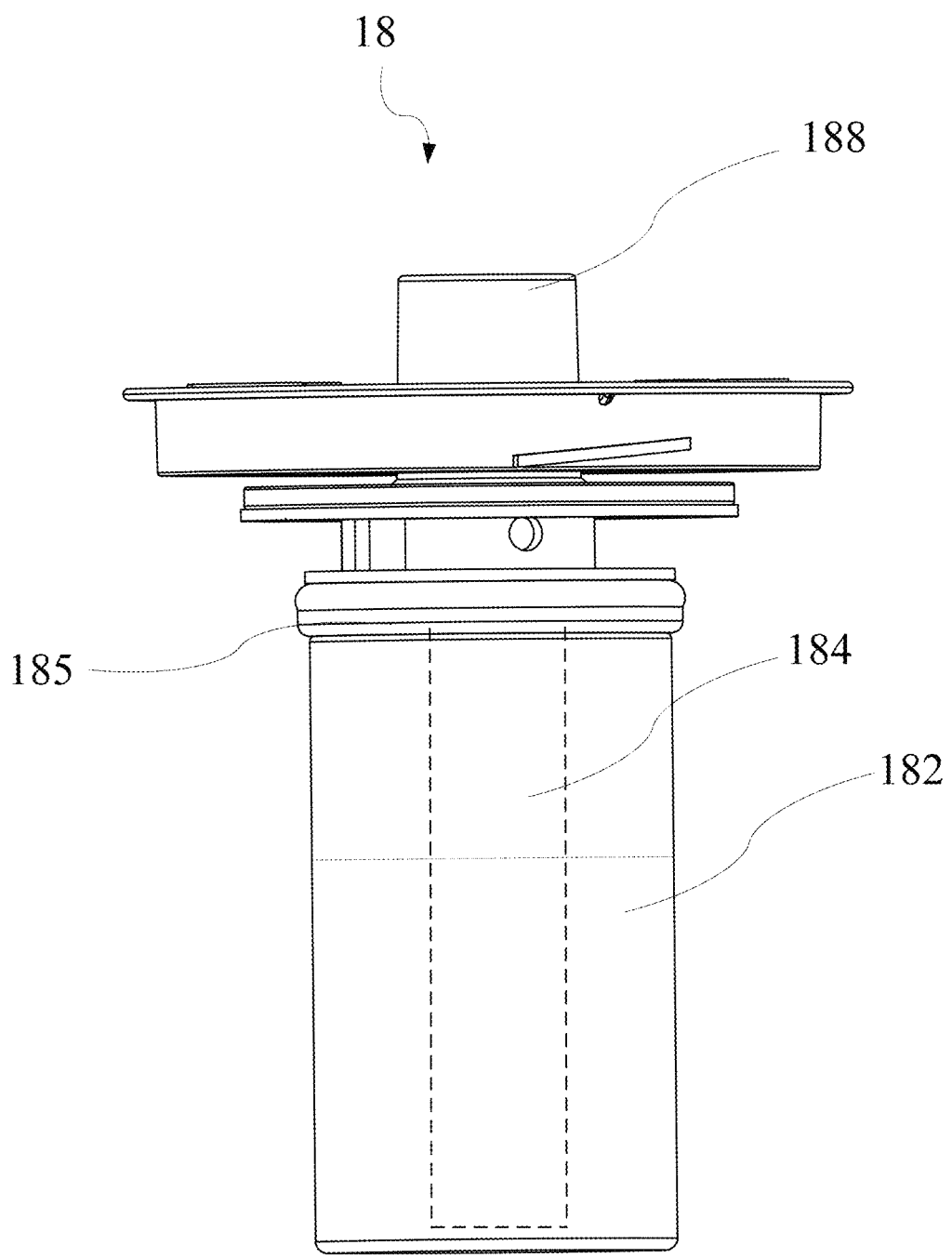
FIG. 8 is a schematic diagram illustrating the nebulizer according to an embodiment of the present invention.

Please refer to FIG. 7 and FIG. 8. FIG. 7 is a cross-sectional diagram illustrating another view of the ion-exchange membrane electrolysis device according to FIG. 6. FIG. 8 is a schematic diagram illustrating the nebulizer according to an embodiment of the present invention. In an embodiment, the plurality of setting structures further includes a fourth setting structure 138. The fourth setting structure 138 is coupled with the third accommodating structure 136, the first setting structure 132 and the second accommodating structure 135 through the gas flow channel system 130. The ion-exchange membrane electrolysis device 1 further includes the nebulizer 18 detachably fastened in the fourth setting structure 138. The nebulizer 18 receives the gas comprising hydrogen from the filter 16 through the third flow channel 1368 of the gas flow channel system 130. The nebulizer 18 selectively generates an atomizing gas, and outputs the diluted gas comprising hydrogen and the atomizing gas through an output port 188 of the nebulizer 18.

The nebulizer 18 accommodates a liquid to be atomized 182 for atomizing the liquid to be atomized 182 into the atomizing gas. The nebulizer 18 includes a cotton column 184 and a microporous vibrating plate 185. One end of the cotton column 184 is immersed in the liquid to be atomized 182 for absorbing the liquid to be atomized 182 to wet the entire cotton column 184. The microporous vibrating plate 185 surrounds the other end of the cotton column 184 to vibrate the cotton column 184 to generate the atomizing gas. Wherein, the maximum atomization amount of the nebulizer 18 is greater than or equal to 20 mL/hr. Further, the atomizing gas could mix with the gas comprising hydrogen to form a healthy gas. The healthy gas is outputted from the output port 188 for the user to inhale.

By integrating the integrated flow channel device 13 including the third flow channel 1368, the third accommodating structure 136, the filter 16 and the nebulizer 18 are connected to each other without additional pipelines.

Please refer to FIG. 3A, FIG. 3B, FIG. 5 and FIG. 6. FIG. 6 is a cross-sectional diagram illustrating the ion-exchange membrane electrolysis device according to FIG. 2. In an embodiment, the first setting structure has the hydrogen input port 1322, oxygen input port 1324 and water output port 1326 respectively connected with the gas flow channel system 131 and the water flow channel system 130. The oxygen input port 1324 and water output port 1326 are connected with the water tank structure 139 through the water flow channel system 131 and the hydrogen input port 1322 is connected with the second accommodating structure 134 through the gas flow channel system 131.

Wherein, the ion-exchange membrane electrolytic cell 12 includes the hydrogen output tube 122 coupled to the hydrogen input port 1322, the oxygen output tube 124 coupled to the oxygen input port 1324 and the water input tube 125 coupled to the water output port 1326. The ion-exchange membrane electrolysis cell 12 also generates the gas comprising oxygen with thermal energy when the water is electrolyzed. The integrated flow channel device 13 further comprises a preheating sink structure 137 connected to the water flow channel system 131, and connected to the water tank structure 139 and the first setting structure 132 through the water flow channel system 131 to be coupled with the ion-exchange membrane electrolysis cell 12. The preheating sink structure 137 receives the water in the water tank structure 139, and replenishes the water through the water outlet port 1326 to the ion-exchange membrane electrolytic cell 12. The preheating sink structure 137 receives the gas comprising oxygen with thermal energy through the oxygen input port 1324. The oxygen output tube 124 is coupled to the oxygen input port 1324 through the water flow channel system 131. The water input tube 126 of the ion-exchange membrane electrolytic cell 12 is coupled to the water output port 1326 through the water output port of the first setting structure 132. The integrated flow channel device 13 further has a longitudinal water tank flow channel 1379 coupled between a water supplement input port 1328 and the water tank structure 139. The water of the water tank structure 139 flows sequentially through the water tank flow channel 1379 and the water supplement input port 1328 to reach to the preheating sink structure 137. When the water contained in the preheating sink structure 137 is reduced by flowing into the ion-exchange membrane electrolytic cell 12, the water of the water tank structure 139 is replenished into the preheating sink structure 137. The oxygen input port 1324 is configured to receive the gas comprising oxygen and thermal energy generated by the ion-exchange membrane electrolytic cell 12. The thermal energy would circulate in the preheating sink structure 137, so that the temperature of the water in the preheating sink structure 137 would be higher than the temperature of the water in the water tank structure 139 in a short time. The preheating sink structure 137 outputs the water to the ion-exchange membrane electrolytic cell 12 through the water output port 1326, so that the high temperature water in the preheating sink structure 137 would be replenished into the ion-exchange membrane electrolytic cell 12 after the ion-exchange membrane electrolytic cell 12 electrolyzes water. Since the ion-exchange membrane electrolytic cell 12 has a higher electrolysis efficiency when electrolyzing water at a suitable high temperature, the provision of the preheating sink structure 137 could rapidly increase the electrolysis efficiency of the ion-exchange membrane electrolytic cell 12. With the integrated flow channel device 13, the hydrogen input port 1322, the oxygen input port 1324, the water supplement input port 1328 and water output port 1326, the devices are connected to each other without additional pipelines.

Figure 15:
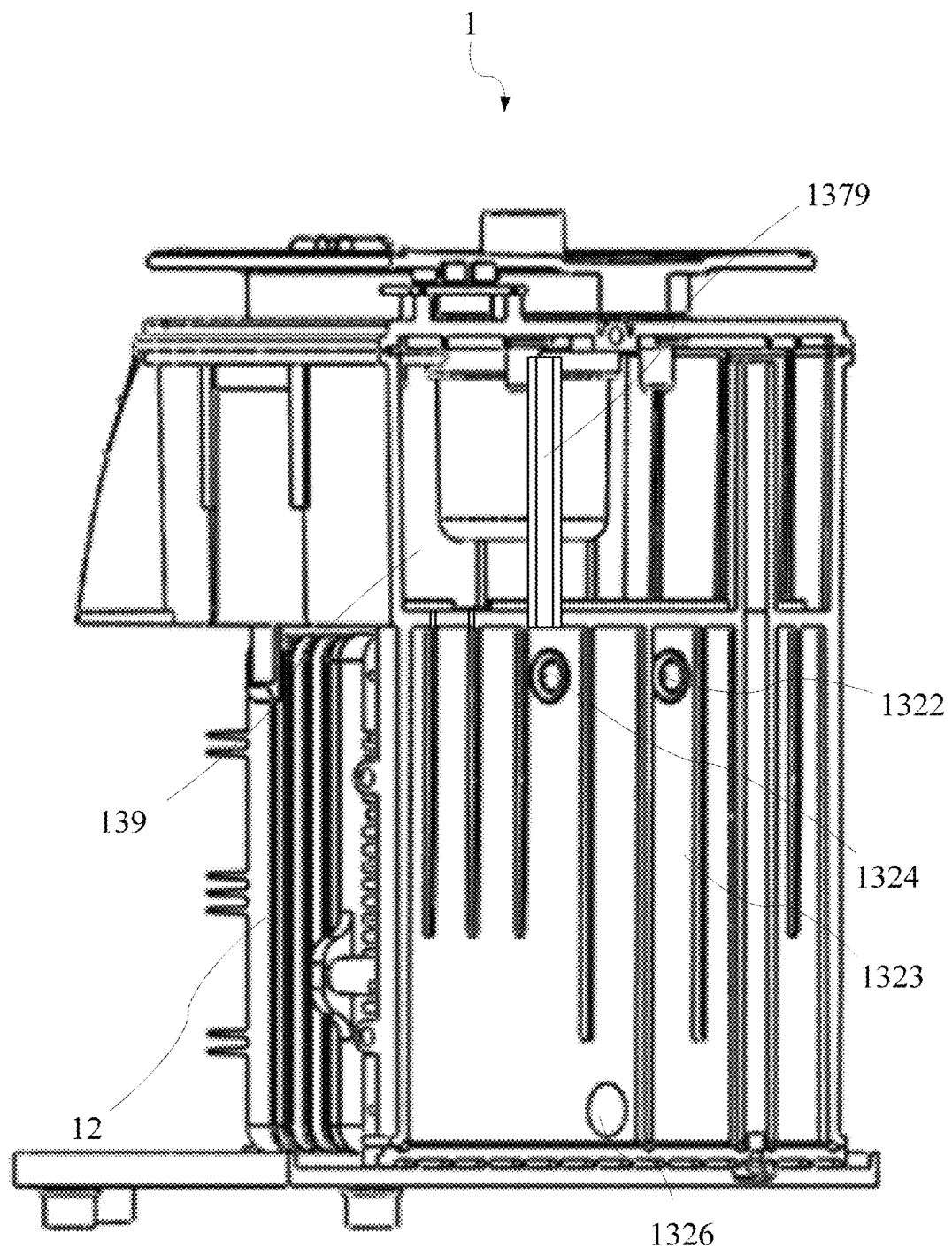
FIG. 15 is a cross-sectional diagram illustrating the ion-exchange membrane electrolysis device according to an embodiment of the present invention.

Please refer to FIG. 3B and FIG. 15. FIG. 15 shows a cross-sectional diagram of the ion-exchange membrane electrolysis device 1 of the present invention. The integrated flow channel device 13 further comprises an oxygen release tube 1378 disposed above the oxygen input port 1324 of the water flow channel system 131 and coupled to the water tank structure 139. One end of the oxygen release tube 1378 protrudes from the water surface in the water tank structure 139, the gas comprising oxygen is released to the atmosphere through the oxygen release tube 1378 through the water tank structure 139. In an embodiment, the water tank structure 139 extends to form a chamber at the same height as the ion-exchange membrane electrolytic cell 12, and the gas comprising oxygen inputted from the oxygen input port 1324 is introduced into the chamber. The chamber communicates with the oxygen release tube 1378, and the oxygen release tube 1378 extends upwardly and above the water level within the water tank structure 139. When the gas comprising oxygen is introduced into the chamber, the gas comprising oxygen is released to the atmosphere through the oxygen release tube 1378.

Further, the water tank structure 139, the preheating sink structure 137, the first setting structure 132, the second accommodating structure 134, the third accommodating structure 135, the water flow channel system 131 and gas flow channel system 130 are integrally formed to form the integrated flow channel device 13. Therefore, the integrated flow channel device 13 could be integrally formed in one piece or partially integrated. In an embodiment, a fifth accommodating structure 135 is formed on the upper cover 133, and the upper cover 133 is independent remaining components of the integrated flow channel device 13. The remaining components and structure of the integrated flow channel device 13 mentioned above are integrally formed to form a main structure, so that the integrated flow channel device 13 could be slightly split into the upper cover 133 and the main structure. Thereby, it is advantageous for the user to replenish water into the water tank structure 139, and the structure of the water flow channel system 131 and the air flow channel system 130 are less affected as well.

Wherein, the above-mentioned setting structure respectively has a fitting structure including a fitting opening, a fitting hole, a fitting tube, a fitting cassette or a fitting clip. In the ion-exchange membrane electrolysis device 1, the ion-exchange membrane electrolytic cell 12 is connected to the oxygen input port 1324 and the water output port 1326 of the integrated flow channel device 13 in a fitting manner. The gas supplement fan 15, the ion-exchange membrane electrolytic cell 12, the filter 16 and the gas-water separator 14 are fitted to the gas flow channel of the integrated flow channel device 13. A simple cassette or a suitable space structure could be designed in the integrated flow channel device 13 or the remaining components mentioned above to facilitate the fitting of the remaining components to the integrated flow channel device 13.

Figure 13:
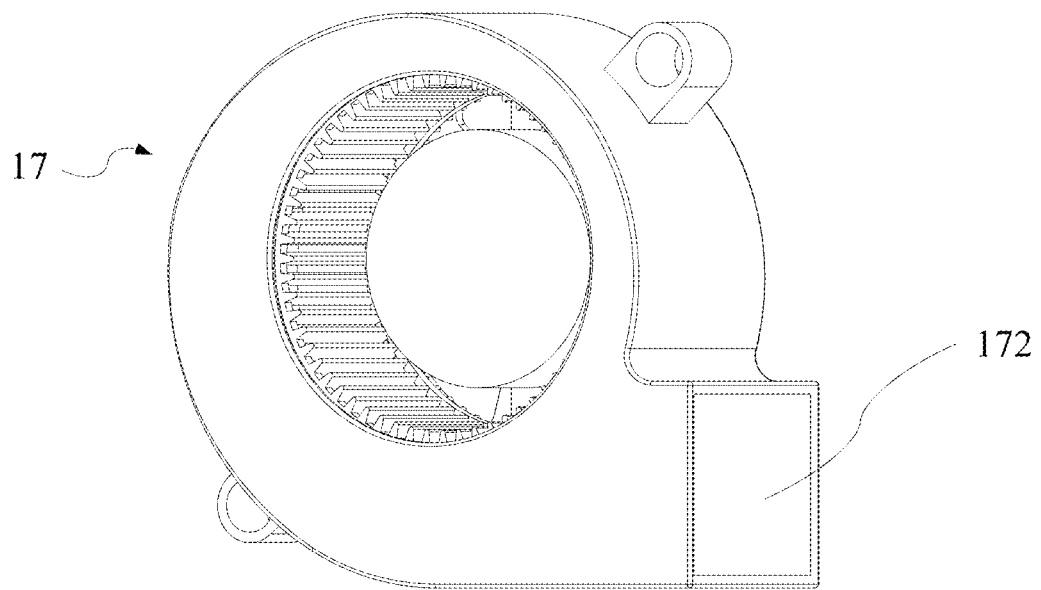
FIG. 13 is a schematic diagram illustrating the cooling fan according to an embodiment of the present invention.

Please refer to FIG. 2 and FIG. 13. FIG. 13 is a schematic diagram illustrating the cooling fan 17 according to an embodiment of the present invention. The ion-exchange membrane electrolysis device 1 of the present invention includes a cooling fan 17 disposed on the integrated flow channel device 13, and the cooling fan 17 drives the external air to flow from a cooling fan port 172 and through the ion-exchange membrane electrolytic cell 12. Therefore, the ion-exchange membrane electrolytic cell 12 could prevent the temperature from being too high and dangerous. In practice, the ion-exchange membrane electrolysis device 1 includes the above-mentioned device and effects, and the maximum using power of the ion-exchange membrane electrolysis device 1 is still less than 240 W.

Figure 14A:
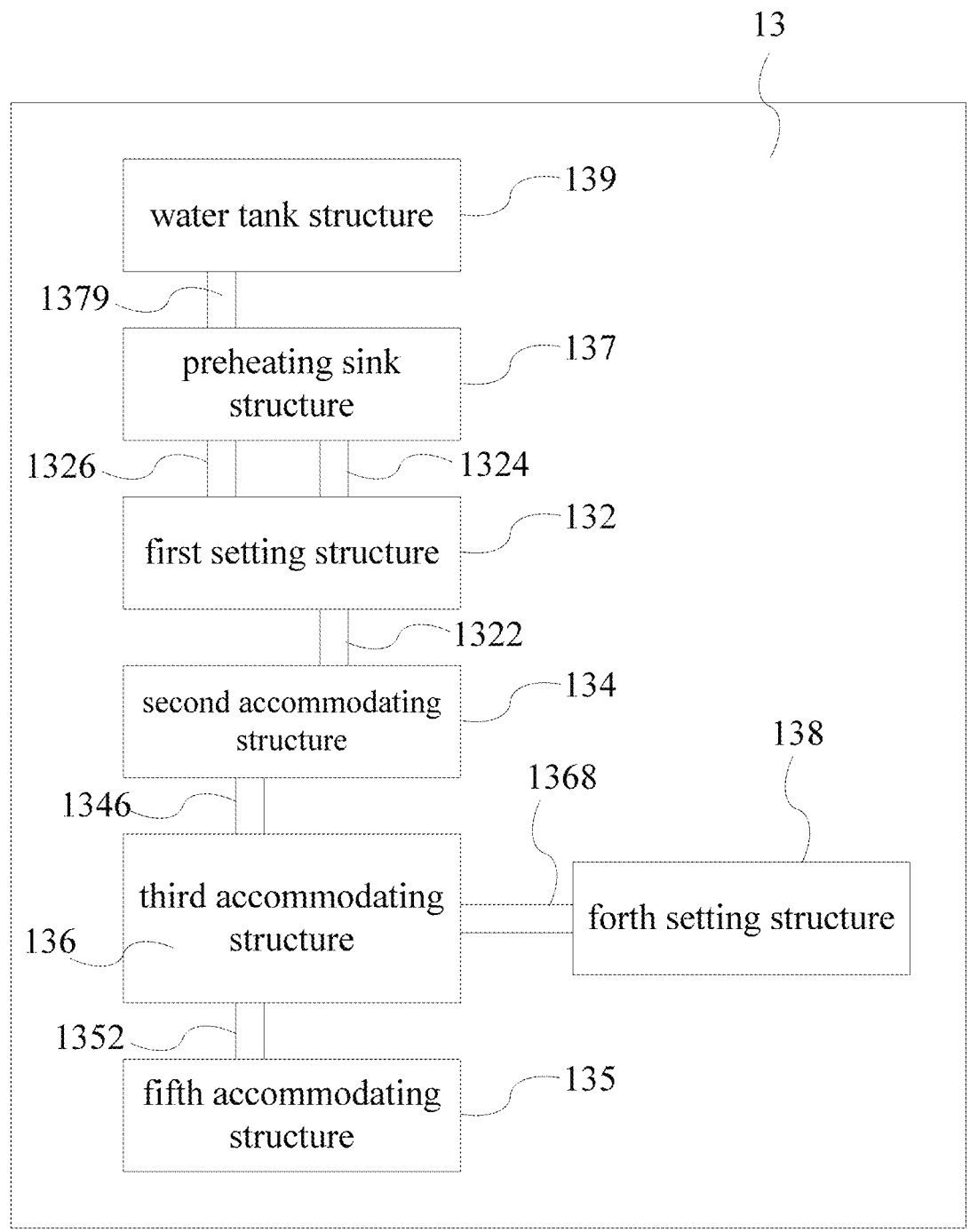
FIG. 14A is an arrangement structure schematic diagram illustrating the integrated flow channel device according to an embodiment of the present invention.
Figure 14B:
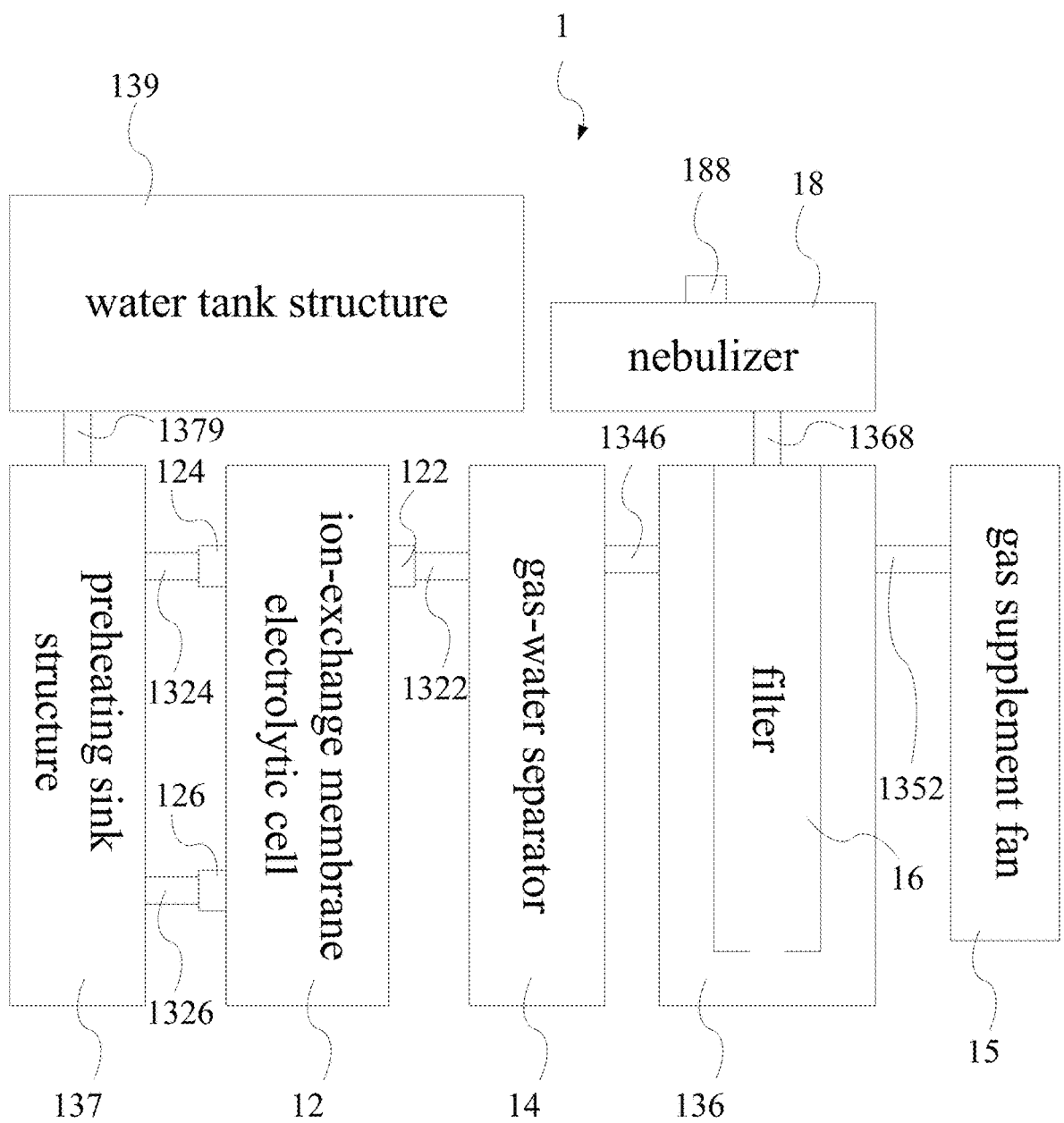
FIG. 14B is a device relationship schematic diagram illustrating the ion-exchange membrane electrolysis device according to an embodiment of the present invention.
Figure 14C:
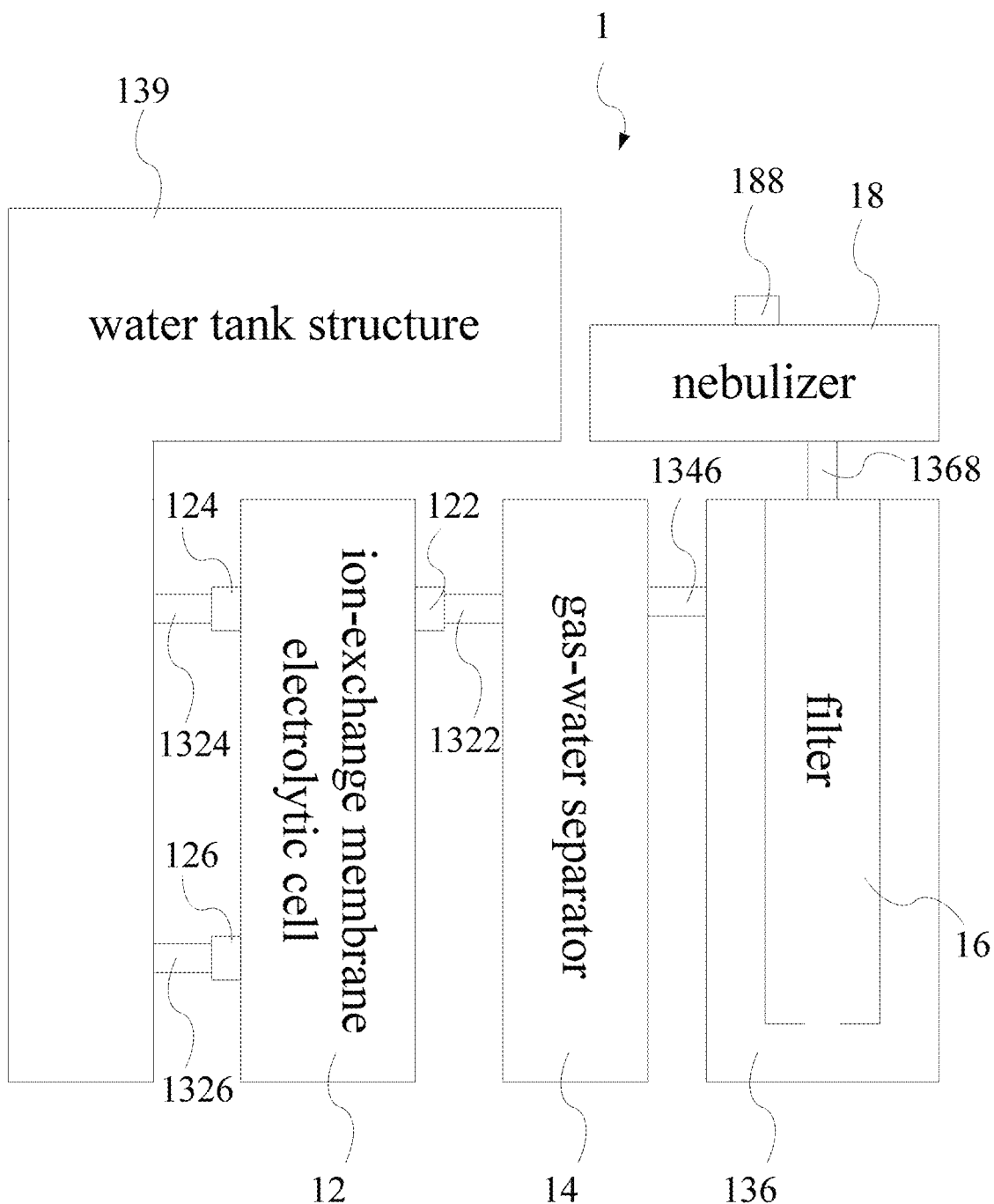
FIG. 14C is a device relationship schematic diagram illustrating the ion-exchange membrane electrolysis device according to an embodiment of the present invention.

Please refer to FIG. 14A, FIG. 14B and FIG. 14C. FIG. 14A is an arrangement structure schematic diagram illustrating the integrated flow channel device according to an embodiment of the present invention. FIG. 14B is a device relationship schematic diagram illustrating the ion-exchange membrane electrolysis device according to an embodiment of the present invention. FIG. 14C is a device relationship schematic diagram illustrating the ion-exchange membrane electrolysis device according to an embodiment of the present invention. In general, the integrated flow channel device 13 includes the plurality of setting structures and flow channels communicating with each other. The water tank structure 139 communicates with the first setting structure 132 through the water tank flow channel 1379, the water output port 1326 and the oxygen input port 1324. The first setting structure 132 communicates with the second accommodating structure 134 through the hydrogen input port 1322. The second accommodating structure 134 communicates with the third accommodating structure 136 through the first flow channel 1346. The fifth accommodating structure 135 communicates with the third accommodating structure 136 through the second flow channel 1352. The third accommodating structure 136 communicates with the forth setting structure 138 through the third flow channel 1368.

The following various devices are incorporated in the integrated flow channel device 13 to form the prototype of the ion-exchange membrane electrolysis device 1 of the present invention. The gas comprising oxygen generated by the ion-exchange membrane electrolytic cell 12 is output from the oxygen output tube 124 to the oxygen input port 1324 of the integrated flow channel device 13, and then enters the preheating sink structure 137 or the water tank structure 139 to be released to atmosphere. The water in the water tank structure 139 could make up the amount of water in the preheating sink structure 137. The water in the preheating sink structure 137 is outputted to the ion-exchange membrane electrolytic cell 12 through the water output port 1326 to supply the water with suitable temperature to the ion-exchange membrane electrolytic cell 12. On the other hand, the gas comprising hydrogen generated by the ion-exchange membrane electrolytic cell 12 is outputted from the hydrogen output tube 122 and enters the gas-water separator 14 to separate the liquid water in the gas comprising hydrogen. The gas comprising hydrogen after separating enters the third accommodating structure 136 through the first flow channel 1346, and the external air introduced by gas supplement fan 15 also enters the third accommodating structure 136 through the second flow channel 1352. The mixing of the two gases could be considered as forming the dilute gas comprising hydrogen which would be inputted to the filter 16 to be filtered. The diluted gas comprising hydrogen after filtering enters the nebulizer 18 through the third flow channel 1368, and mixes with the atomizing gas generated by the nebulizer 18 to form the healthy gas. The healthy gas is outputted from the output port 188 for the user to inhale. The gas flow direction is only in one-way flow direction in principle.

Another objective of the present invention provides the ion-exchange membrane electrolysis device 1 comprising the ion-exchange membrane electrolytic cell 12, the integrated flow channel device 13 and the gas supplement fan 15. The ion-exchange membrane electrolytic cell 12 is configured to electrolyze water to respectively generate the gas comprising hydrogen and the gas comprising oxygen with thermal energy. The gas supplement fan 15 is configured to introduce the external air from outside the ion-exchange membrane electrolysis device 1. The integrated flow channel device 13 further includes the water tank structure 139, the preheating sink structure 137, the plurality of setting structures, the water flow channel system 131, and the air flow channel system 130. The water tank structure 139 is connected to the ion-exchange membrane electrolytic cell 12 through the preheating sink structure 137 for replenishing water to the ion-exchange membrane electrolytic cell 12. The relative position of the water tank structure 139 is higher than that of the ion-exchange membrane electrolytic cell 12, so that the water in the water tank structure 139 is fed downward into the ion-exchange membrane electrolytic cell 12 by gravity or pressure difference. The preheating sink structure 137 has the oxygen input port (not shown in the figures), the water supplement input port (not shown in the figures), and a water output port 1326, wherein the water supplement input port is connected to the water tank structure 139 to receive water in the water tank structure 139, and the water output port 1326 outputs the water in the preheating sink structure 137 to the ion-exchange membrane electrolytic cell 12. The oxygen input port is configured to receive the gas comprising oxygen and the thermal energy generated by the ion-exchange membrane electrolytic cell 12, wherein the thermal energy is configured to heat the water in the preheating sink structure 137. The first setting structure 132 of the plurality of setting structures disposes the ion-exchange membrane electrolytic cell 12 therein. The fifth receiving structure 135 of the plurality of setting structures disposes the gas supplement fan 15 therein. The water flow channel system 131 includes the plurality of flow channels respectively communicating with the water tank structure 139 and the preheating sink structure 137 to input the water from the preheating sink structure 137 to the ion-exchange membrane electrolytic cell 12, and to output the gas comprising oxygen with thermal energy from the ion-exchange membrane electrolytic cell 12 to the preheating sink structure 137. The gas flow channel system 130 includes the plurality of flow channels respectively communicating with the plurality of setting structures to receive the gas comprising hydrogen and the external air and mix the gas comprising hydrogen with the external air to form the diluted gas comprising hydrogen. The hydrogen concentration of the diluted gas comprising hydrogen is equal to 4% or less.

In another embodiment, the ion-exchange membrane electrolysis device 1 of the present invention comprises the ion-exchange membrane electrolytic cell 12 and the integrated flow channel device 13. The ion-exchange membrane electrolytic cell 12 is configured for electrolyzing water to generate the gas comprising hydrogen and the gas comprising oxygen. The integrated flow channel device 13 is integrally formed, and further includes the water tank structure 139, the first setting structure 132, the water flow channel system 131, the gas flow channel system 130, the fifth accommodating structure 135, and the preheating sink structure 137. The water tank structure 139 is configured to accommodate water. The first setting structure 132 has the hydrogen input port 1322, the oxygen input port 1324, and the water output port 1326. The first setting structure 132 is configured to detachably secure the ion-exchange membrane electrolytic cell 12 to the integrated flow channel device 13. The water flow channel system 131 communicates with the water tank structure 139 and the first setting structure 132 to input water from the water tank structure 139 to the ion-exchange membrane electrolytic cell 12. The gas flow channel system 130 is coupled to the first setting structure 132 to receive the gas comprising hydrogen generated by the ion-exchange membrane electrolytic cell 12. The preheating sink structure 137 is coupled to the water tank structure 139 and the first setting structure 132. The water in the water tank structure 139 can be inputted to the ion-exchange membrane electrolytic cell 12 through the preheating sink structure 137 and the water output port 1326 of the first setting structure 132. The water tank structure 139 is coupled to the water output port 1326 by the water flow channel system 131 and the preheating sink structure 137. The gas flow channel system 130 receives the gas comprising hydrogen generated by the ion-exchange membrane electrolytic cell 12 through the hydrogen input port 1322. The ion-exchange membrane electrolysis device 1 further includes a gas supplement fan 15 detachably fastened to the fifth accommodating structure 135 for introducing the external air to be mixed with the gas comprising hydrogen to generate a first mixed gas. The ion-exchange membrane electrolysis device 1 further includes the nebulizer 18 extending into the water tank structure 139. The nebulizer 18 selectively generates an atomizing gas and mixes the first mixed gas with the atomizing gas after receiving the first mixed gas to output an atomized gas comprising hydrogen. The ion-exchange membrane electrolysis device 1 includes an operation panel. The user could adjust the total amount of the gas comprising hydrogen outputted from the ion-exchange membrane electrolysis device 1 by the operation panel. In an embodiment, the volume of the ion-exchange membrane electrolysis device 1 is less than 15 liters, and the maximum using power of the ion-exchange membrane electrolysis device 1 is less than 240 W. The total amount of the atomized gas comprising hydrogen outputs in this embodiment can be set between 2 L/min and 6 L/min, for example, 2 L/min, 4 L/min or 6 L/min. The ion-exchange membrane electrolysis device 1 could be adjusted by the operation panel to the concentration of the outputted gas comprising hydrogen equal to 4% or less.

In another embodiment, the ion-exchange membrane electrolysis device 1 of the present invention includes the ion-exchange membrane electrolytic cell 12, the integrated flow channel device 13, and the nebulizer 18. The ion-exchange membrane electrolytic cell 12 is configured for electrolyze water to generate the gas comprising hydrogen. The integrated flow channel device 13 further includes the water tank structure 139, the plurality of setting structures, and the water flow channel system 131. The water tank structure 139 is in communication with the ion-exchange membrane electrolysis cell 12 for replenishing water to the ion-exchange membrane electrolytic cell 12. The first setting structure 132 of the plurality of setting structures detachably locks the ion-exchange membrane electrolytic cell 12 therein. The fourth setting structure 138 of the plurality of setting structures detachably holds the nebulizer 18 therein. The water flow channel system 131 includes the plurality of flow channels respectively communicating with the water tank structure 139 to replenish water in the water tank structure 139 into the ion-exchange membrane electrolytic cell 12. The gas flow channel system 130 delivers the gas comprising hydrogen to the nebulizer 18. The nebulizer 18 is coupled to the ion-exchange membrane electrolytic cell 12 to receive the gas comprising hydrogen. The nebulizer 18 is configured to generate the atomizing gas. The gas comprising hydrogen is mixed with the atomizing gas to form the healthy gas. The healthy gas is output via the output port 188 of the nebulizer 18. The hydrogen concentration of the healthy gas outputted from the nebulizer 18 equal to 99% or more.

In another embodiment, the ion-exchange membrane electrolysis device 1 of the present invention comprises the ion-exchange membrane electrolytic cell 12 which is configured for electrolyzing water to generate the gas comprising hydrogen and the gas comprising oxygen. The ion-exchange membrane electrolysis device 1 also comprises the integrated flow channel device 13 integrally formed, the water tank structure 139, the first setting structure 132, the water flow channel system 131, and the gas flow channel system 130. The water tank structure 139 is configured to accommodate water. The first setting structure 132 is configured to detachably secure the ion-exchange membrane electrolytic cell 12 to the integrated flow channel device 13. The water flow channel system 131 communicates with the water tank structure 139 and the first setting structure 132 to input water from the water tank structure 139 to the ion-exchange membrane electrolytic cell 12. The gas flow channel system 130 is coupled to the first setting structure 132 to receive the gas comprising hydrogen generated by the ion-exchange membrane electrolytic cell 12. The first setting structure 132 has the hydrogen input port 1322, the oxygen input port 1324, and the water output port 1326. The water tank structure 139 is coupled to the water output port 1326 through the water flow channel system 131 and the preheating sink structure 137. The gas flow channel system 130 receives the gas comprising hydrogen generated by the ion-exchange membrane electrolytic cell 12 through the hydrogen input port 1322. The ion-exchange membrane electrolytic cell 12 further includes the upper cover 133 and the nebulizer 18. The upper cover 133 is disposed on the water tank structure 139. The upper cover 133 further has the fourth setting structure 138. The nebulizer 18 is detachably fastened to the fourth setting structure 138 and extends into the water tank structure 139. The nebulizer 18 selectively generates the atomizing gas, and after receiving the gas comprising hydrogen, the gas comprising hydrogen is mixed with the atomizing gas to output the atomized gas comprising hydrogen. The volume of the ion-exchange membrane electrolysis device 1 is less than 13 liters, and the maximum using power of the ion-exchange membrane electrolysis device 1 is less than 400 W. The total amount of gas comprising hydrogen output in this embodiment is between 400 mL/min and 600 mL/min. For example, it could be set in 400 mL/min, 500 mL/min, or 600 mL/min. The ion-exchange membrane electrolysis device 1 could be adjusted by the operation panel so that the hydrogen concentration of the gas comprising hydrogen equal to 99% or more.

In summary, the gas flow channel system has the first flow channel, the third flow channel, the second flow channel, and the hydrogen input port for transporting hydrogen in the ion-exchange membrane electrolysis device to each device in each setting structure, such as the ion-exchange membrane electrolytic cell, the filter, the nebulizer, and the gas supplement fan. The water flow channel system has the water tank flow channel, the water supplement input port, the water output port and the oxygen input port for connecting the water tank structure with the ion-exchange membrane electrolytic cell. The design of the gas flow channel system and the water flow channel system replaces the additional pipelines, allowing the ion-exchange membrane electrolysis device to communicate with each of setting structures through these channels to simplify the piping in the production process and reduces pipe consumables and labor costs. The reserved space of the setting structures easily rescues other devices to the integrated flow channel device, such as the ion-exchange membrane electrolytic cell, the filter, the nebulizer, and the gas supplement fan, so that the devices can be stably disposed in the ion-exchange membrane electrolysis device. More importantly, the integrated flow channel device integrates the complicated pipelines of the ion-exchange membrane electrolysis device, reduces the reserved space for the ion-exchange membrane electrolysis device, optimizes space utilization, and reduces the possibility of water leaking and gas leaking to improve operational safety of the ion-exchange membrane electrolysis device.

Compare to the prior art, the integrated flow channel device conducts a gas path or a water path among various components, avoiding additional pipe connections, functionally integrating independent devices and pipes to optimize space utilization, reducing the manufacturing cost and the volume required for the ion-exchange membrane electrolysis device and improving the operational safety of the ion-exchange membrane electrolysis device and the intuitiveness of assembly. In addition, the water in the preheating sink structure receives the thermal energy generated by the ion-exchange membrane electrolytic cell, and the high temperature water is sent to the ion-exchange membrane electrolytic cell, so that the water in the ion-exchange membrane electrolytic cell is maintained at an appropriate working temperature, thereby improving electrolysis efficiency. At the same time, the gas flow channel system and the water flow channel system preset between the respective setting structures to transport gas and liquid. Therefore, it is not necessary to additionally connect the pipeline between the devices, so that the hose or the wire-like pipeline is reduced to avoid the occupation of space and the entanglement or the misconnection of pipelines, and, the wiring cost is also saved. In addition, the danger of hidden pipelines falling out in the prior art is avoided, and the possibility of water leakage or air leakage is reduced. More importantly, each function-independent device is integrated through the integrated flow channel device to optimize space utilization. Therefore, the present invention facilitates the design, manufacture, installation or maintenance of the ion-exchange membrane electrolysis device, and also reduces the additional piping.

With the examples and explanations mentioned above, the features and spirits of the invention are hopefully well described. More importantly, the present invention is not limited to the embodiment described herein. Those skilled in the art will readily observe that numerous modifications and alterations of the device may be made while retaining the teachings of the invention. Accordingly, the above disclosure should be construed as limited only by the metes and bounds of the appended claims.

What is claimed is:

1. An ion-exchange membrane electrolysis device, comprising:
an ion-exchange membrane electrolysis cell configured to electrolyze water to produce a gas comprising hydrogen and a gas comprising oxygen; and
an integrated flow channel device including:
a water tank structure configured for accommodating water;
a first setting structure configured for detachably fastening the ion-exchange membrane electrolysis cell to the integrated flow channel device;
a water flow channel system coupled to the water tank structure and the first setting structure to input the water from the water tank structure to the ion-exchange membrane electrolysis cell; and
a gas flow channel system coupled to the first setting structure to receive the gas comprising hydrogen generated by the ion-exchange membrane electrolysis cell;
wherein the first setting structure has a hydrogen input port, an oxygen input port and a water output port, the water tank structure is coupled to the water output port through the water flow channel system, so that water in the water tank structure can be input to the ion-exchange membrane electrolysis cell, the gas flow channel system receives the gas comprising hydrogen generated by the ion-exchange membrane electrolysis cell through the hydrogen input port, and the oxygen input port is coupled to the water flow channel system and the water tank structure.

2. The ion-exchange membrane electrolysis device of the claim 1, wherein the integrated flow channel device further comprises a second accommodating structure for accommodating a gas-water separator, the gas-water separator is coupled to the first setting structure through the gas flow channel system, the gas-water separator receives the gas comprising hydrogen generated by the ion-exchange membrane electrolysis cell and retains liquid water of the gas comprising hydrogen, and then outputs the gas comprising hydrogen through the gas flow channel system.

3. The ion-exchange membrane electrolysis device of the claim 1, wherein the integrated flow channel device further comprises a second accommodating structure for accommodating a bobber and a spring valve; wherein the second accommodating structure receives the gas comprising hydrogen generated by the ion-exchange membrane electrolysis cell and retains liquid water of the gas comprising hydrogen, when the liquid water accommodated in the second accommodating structure reaches to a water level, the bobber blocks the gas comprising hydrogen from passing to the gas flow channel system, when the gas pressure of the gas comprising hydrogen in the second accommodating structure is equal to a pressure threshold, the spring valve is opened to connect the second accommodating structure and the gas flow channel system, and then the gas comprising hydrogen is outputted through the gas flow channel system.

4. The ion-exchange membrane electrolysis device of the claim 1, wherein the ion-exchange membrane electrolysis cell has a first side and includes a hydrogen output tube coupled to the hydrogen input port, an oxygen output tube coupled to the oxygen input port, and a water input tube coupled to the water output port; the oxygen output tube and the hydrogen input tube respectively output the gas comprising oxygen and the gas comprising hydrogen to the oxygen input port and hydrogen input port from the first side of the ion-exchange membrane electrolysis cell, and the water input tube receives the water from the water tank structure at the first side through the water output port.

5. The ion-exchange membrane electrolysis device of the claim 1, wherein the integrated flow channel device further comprises a preheating sink structure coupled to the water tank structure and the first setting structure; the water in the water tank structure can be input to the ion-exchange membrane electrolysis cell through the preheating sink structure and the water output port of the first setting structure, and the preheating sink structure is further coupled to the oxygen input port to receive the gas comprising oxygen.

6. The ion-exchange membrane electrolysis device of the claim 1, wherein the integrated flow channel device further comprises an oxygen release tube disposed above the oxygen input port in the water flow channel system and coupled to the water tank structure, the gas comprising oxygen is released to the atmosphere through the oxygen release tube through the water tank structure.

7. The ion-exchange membrane electrolysis device of the claim 1, wherein the integrated flow channel device further comprises a third accommodating structure, the ion-exchange membrane electrolysis device further comprises a filter detachably fastened in the third accommodating structure, the filter receives the gas comprising hydrogen through the gas flow channel system and filters the gas comprising hydrogen.

8. The ion-exchange membrane electrolysis device of the claim 1, wherein a lower end of the filter has a filter input port to receive the gas comprising hydrogen and an upper end of the filter has a filter output port to output the filtered gas comprising hydrogen, the filter includes a filter core, and the filter input port is coupled to the filter output port via the filter core, wherein the filter and the third accommodating structure block the filter input port be coupled to the filter output port via the third accommodating structure.

9. The ion-exchange membrane electrolysis device of the claim 1, further comprising an upper cover and a nebulizer, the upper cover disposed on the water tank structure of the integrated flow channel device, the upper cover further including a fourth setting structure, the nebulizer detachably fastened to the fourth setting structure and extended into the water tank structure, the nebulizer configured to selectively generate an atomizing gas and after receiving the gas comprising hydrogen, the nebulizer mixes the gas comprising hydrogen with the atomizing gas and then output the mixed gas.

10. The ion-exchange membrane electrolysis device of the claim 9, wherein the nebulizer accommodates a liquid to be atomized, and the nebulizer including a cotton column and a microporous vibrating plate, one end of the cotton column is immersed in the liquid to be atomized to absorb the liquid to be atomized, and the microporous vibrating plate surrounds the other end of the cotton column to atomize the liquid to be atomized absorbed by the cotton column to generate the atomizing gas.

11. The ion-exchange membrane electrolysis device of the claim 1, wherein the integrated flow channel device further comprises a fifth accommodating structure located in the integrated flow channel device, the fifth accommodating structure is coupled to the gas flow channel system; the ion-exchange membrane electrolysis device further includes a gas supplement fan detachably fastened to the fifth accommodating structure; the gas supplement fan is configured to introduce an external air to be mixed with the gas comprising hydrogen.

12. The ion-exchange membrane electrolysis device of the claim 1, wherein the relative position of the water tank structure is higher than that of the ion-exchange membrane electrolysis cell.

13. An ion-exchange membrane electrolysis device, comprising:
an ion-exchange membrane electrolysis cell configured to electrolyze water to produce a gas comprising hydrogen and a gas comprising oxygen; and
an integrated flow channel device including:
a water tank structure configured for accommodating water;
a first setting structure configured for detachably fastening the ion-exchange membrane electrolysis cell to the integrated flow channel device and including a hydrogen input port, an oxygen input port and a water output port;
a water flow channel system coupled to the water tank structure and first setting structure to input the water from the water tank structure to the ion-exchange membrane electrolysis cell;
a gas flow channel system coupled to the first setting structure to receive the gas comprising hydrogen generated by the ion-exchange membrane electrolysis cell;
a fifth accommodating structure, and
a preheating sink structure coupled to the water tank structure and the first setting structure, the water in the water tank structure being inputted to the ion-exchange membrane electrolysis cell through the preheating sink structure and the water output port of the first setting structure;
wherein the water tank structure is coupled to the water output port through the water flow channel system and the preheating sink structure, the gas flow channel system receives the gas comprising hydrogen generated by the ion-exchange membrane electrolysis cell through the hydrogen input port;
wherein the ion-exchange membrane electrolysis device further includes a gas supplement fan detachably fastened to the fifth accommodating structure, the gas supplement fan is configured to introduce an external air to be mixed with the gas comprising hydrogen to generate a first mixed gas;
wherein the ion-exchange membrane electrolysis device further includes a nebulizer extending into the water tank structure, the nebulizer is configured to selectively generate an atomizing gas, and mix the first mixed gas with the atomizing gas to output the atomizing gas comprising hydrogen after receiving the first mixed gas.

14. The ion-exchange membrane electrolysis device of the claim 13, wherein the ion-exchange membrane electrolysis cell has a first side and includes a hydrogen output tube coupled to the hydrogen input port, an oxygen output tube coupled to the oxygen input port, and a water input tube coupled to the water output port; wherein the hydrogen output tube, the oxygen output tube, and the water input tube are disposed on the first side.

15. The ion-exchange membrane electrolysis device of the claim 13, further comprising an operation panel, wherein the operation panel is configured to adjust the flow rate of the atomizing gas comprising hydrogen to be outputted by the ion-exchange membrane electrolysis device to a range between 2 L/min and 6 L/min.

16. The ion-exchange membrane electrolysis device of the claim 13, wherein the concentration of the atomizing gas comprising hydrogen is less than 4%, the volume of the ion-exchange membrane electrolysis device is less than 15 liters, and the maximum using power of the ion-exchange membrane electrolysis device is less than 240 W.

17. An ion-exchange membrane electrolysis device, comprising:
an ion-exchange membrane electrolysis cell configured to electrolyze water to produce a gas comprising hydrogen and a gas comprising oxygen; and
an integrated flow channel device including:
a water tank structure configured for accommodating water;
a first setting structure configured for detachably fastening the ion-exchange membrane electrolysis cell to the integrated flow channel device;
a water flow channel system coupled to the water tank structure and first setting structure to input the water from the water tank structure to the ion-exchange membrane electrolysis cell; and
a gas flow channel system coupled to the first setting structure to receive the gas comprising hydrogen generated by the ion-exchange membrane electrolysis cell;
wherein the first setting structure has a hydrogen input port, an oxygen input port and a water output port, the water tank structure is coupled to the water output port through the water flow channel system, the gas flow channel system receives the gas comprising hydrogen generated by the ion-exchange membrane electrolysis cell through the hydrogen input port;
wherein the ion-exchange membrane electrolysis device further comprising an upper cover and a nebulizer, the upper cover is disposed on the water tank structure and further comprises a fourth setting structure, the nebulizer detachably fastened to the fourth setting structure and extended into the water tank structure, the nebulizer is configured to selectively generate an atomizing gas, mix the gas comprising hydrogen mixed with the atomizing gas after receive the gas comprising hydrogen, and then output an atomizing gas comprising hydrogen.

18. The ion-exchange membrane electrolysis device of the claim 17, further comprising an operation panel, wherein the operation panel is configured to adjust the flow rate of the atomizing gas comprising hydrogen to be outputted by the ion-exchange membrane electrolysis device to a range between 400 mL/min and 600 mL/min.

19. The ion-exchange membrane electrolysis device of the claim 17, wherein the concentration of the outputted atomizing gas comprising hydrogen is more than 99%, the volume of ion-exchange membrane electrolysis device is less than 13 liters, and the maximum using power of the ion-exchange membrane electrolysis device is less than 400 W.

20. The ion-exchange membrane electrolysis device of the claim 17, wherein the oxygen input port is coupled to the water flow channel system and coupled with the water tank structure, the integrated flow channel device further comprises an oxygen release tube disposed above the oxygen input port in the water flow channel system and coupled to the water tank structure, the gas comprising oxygen is released to the atmosphere through the oxygen release tube through the water tank structure.

* * * * *